(12) United States Patent
Faour et al.

(10) Patent No.: US 8,029,822 B2
(45) Date of Patent: *Oct. 4, 2011

(54) RUPTURING CONTROLLED RELEASE DEVICE HAVING A PREFORMED PASSAGEWAY

(75) Inventors: Joaquina Faour, Buenos Aires (AR); Juan A Vergez, Buenos Aires (AR)

(73) Assignee: Osmotica Kereskedelmi és Seolgáltató KFT, Budapest (HU)

(*) Notice: Subject to any disclaimer, the term of this patent is extended or adjusted under 35 U.S.C. 154(b) by 736 days.

This patent is subject to a terminal disclaimer.

(21) Appl. No.: 10/851,866

(22) Filed: May 21, 2004

(65) Prior Publication Data

US 2005/0008702 A1    Jan. 13, 2005

Related U.S. Application Data

(60) Provisional application No. 60/472,819, filed on May 22, 2003.

(51) Int. Cl.
*A61K 9/48* (2006.01)
(52) U.S. Cl. ........................ 424/463; 424/473
(58) Field of Classification Search ................ 424/463, 424/473
See application file for complete search history.

(56) References Cited

U.S. PATENT DOCUMENTS

| | | | |
|---|---|---|---|
| 3,247,066 A | 4/1966 | Mllosovich, Jr. | |
| 3,845,770 A | 11/1974 | Theeuwes et al. | 128/260 |
| 3,916,899 A | 11/1975 | Theeuwes et al. | |
| 3,952,741 A | 4/1976 | Baker | |
| 4,014,334 A | 3/1977 | Theeuwes et al. | 424/427 |
| 4,016,880 A | 4/1977 | Theeuwes et al. | |
| 4,088,864 A | 5/1978 | Theeuwes et al. | 219/121.7 |
| 4,271,113 A | 6/1981 | Luschen | |
| 4,576,604 A | 3/1986 | Guittard et al. | 424/473 |
| 4,608,048 A | 8/1986 | Cortese et al. | 604/890 |
| 4,673,405 A | 6/1987 | Guittard et al. | 424/473 |
| 4,801,461 A | 1/1989 | Hamel et al. | 424/467 |
| 4,810,502 A * | 3/1989 | Ayer et al. | 424/473 |
| 5,358,502 A | 10/1994 | Herbig et al. | 604/892.1 |
| 5,417,682 A * | 5/1995 | Wong et al. | 604/892.1 |
| 5,516,527 A | 5/1996 | Curatolo | |
| 5,524,907 A * | 6/1996 | Walser | 277/640 |
| 5,558,879 A * | 9/1996 | Chen et al. | 424/480 |
| 5,609,590 A | 3/1997 | Herbig et al. | 604/892.1 |
| 5,681,584 A | 10/1997 | Savastano et al. | |
| 5,792,471 A | 8/1998 | Curatolo | |
| 5,837,379 A * | 11/1998 | Chen et al. | 424/465 |
| 5,840,335 A | 11/1998 | Wenzel et al. | |
| 5,876,750 A | 3/1999 | Jao et al. | |
| 5,882,682 A * | 3/1999 | Rork et al. | 424/473 |
| 5,914,131 A * | 6/1999 | Merrill et al. | 424/473 |
| 6,004,582 A * | 12/1999 | Faour et al. | 424/473 |
| 6,365,185 B1 * | 4/2002 | Ritschel et al. | 424/473 |
| 6,599,284 B2 | 7/2003 | Faour et al. | 604/892.1 |
| 6,632,451 B2 * | 10/2003 | Penhasi et al. | 424/464 |
| 2002/0086054 A1 | 7/2002 | Shaw | |
| 2002/0099361 A1 * | 7/2002 | Faour | 604/892.1 |

FOREIGN PATENT DOCUMENTS

| | | |
|---|---|---|
| EP | 0378404 | 7/1990 |
| WO | W00152819 | 7/2001 |
| WO | WO 02/080887 A2 | 10/2002 |

OTHER PUBLICATIONS

Chem Pharm Bull.47 (7)939-943 (1999).*
Heng, Paul Wan Sia et al.; Mechanism of Pellet Coat Rupture and Its Effect on Drug Release; Chem. Pharm. Bull., 1999; 47 (7) 939-943.

* cited by examiner

*Primary Examiner* — Gollamudi Kishore
*Assistant Examiner* — Snigdha Maewall
(74) *Attorney, Agent, or Firm* — Rick Matos; Innovar, L.L.C.

(57) ABSTRACT

The present invention provides a simple and improved osmotic device that is capable of providing a controlled release of active agent contained in the core first through a preformed passageway and then through an in situ formed second passageway into an environment of use. One or both of the passageways optionally increases in size during use of the osmotic device. The preformed passageway and/or the second passageway increase the release rate of the active agent, enable the release of large particles containing active agent, and/or enable the release of active agents that are substantially insoluble in the environment of use. By virtue of the in situ formation of the second aperture, the device is able to release a greater overall percentage of active agent than it would release in absence of the second aperture.

60 Claims, 3 Drawing Sheets

RUPTURING CONTROLLED RELEASE DEVICE HAVING A PREFORMED PASSAGEWAY

CROSS-REFERENCE TO EARLIER FILED APPLICATIONS

The present application claims the benefit of priority of Provisional Application for Patent No. 60/472,819 filed May 22, 2003 in the name of the above-named inventors, the entire disclosure of which is hereby incorporated by reference.

FIELD OF THE INVENTION

This invention pertains to a drug delivery device for the controlled delivery of a maximum amount of active agent to an environment of use. More particularly, it pertains to a controlled release drug delivery device comprising a wall that ruptures during use even though the wall has at least one preformed aperture, the rupture occurring at a location spaced away from the preformed aperture.

BACKGROUND OF THE INVENTION

Osmotic devices have demonstrated utility in delivering useful active agents such as medicines, nutrients, food products, pesticides, herbicides, germicides, algaecides, chemical reagents, and others known to those of ordinary skill to an environment of use in a controlled manner over prolonged periods of time. Known devices include tablets, pastilles, pills or capsules and others that use osmotic pressure to control the release of the active agent contained in the core of the osmotic device. Some osmotic devices may also include layers comprising one or more materials that are subject to erosion or that slowly dissolve in the environment of use thereby gradually dispensing the active agent. Known devices generally suffer from an inability to dispense all or substantially all the active agent from the core prior to the loss of osmotic pressure that occurs at osmotic equilibrium.

U.S. Pat. No. 4,088,864 to Theeuwes et al. ("Theeuwes et al. '864) discloses a high speed process for forming outlet passageways in the walls of osmotic devices for release of the contents of the osmotic device comprising: a) moving the pills in succession along a predetermined path at a predetermined velocity; b) tracking the moving pills seriatim at said velocity with a laser of a wavelength which is absorbable by said walls by oscillating the optical path of the laser back and forth over a predetermined section of the pill path at said velocity; c) firing the laser during said tracking; d) adjusting the laser beam dimension at said wall, the laser power and the firing duration such that the laser beam is capable of piercing the wall; and e) forming, with the laser beam, an outlet passageway 4 to 2000 microns in diameter in the wall. Theeuwes et al. '864 does not disclose an osmotic device which membrane ruptures even though it has a preformed aperture in the membrane.

Theeuwes et al. '864 also discloses an apparatus for forming outlet passageways in the walls of osmotic devices for release of the contents of the osmotic device comprising: a) a support frame; b) a laser operating in a pulse mode; c) an optical pill tracking mechanism; d) a rotary pill indexer; and e) an electrical power supply to supply and control power for the laser, the tracking mechanism, and the indexer. Theeuwes et al. '864 does not disclose an osmotic device which membrane ruptures even though it has a preformed aperture in the membrane.

U.S. Pat. No. 4,014,334 to Theeuwes et al. ("Theeuwes et al. '334") discloses an osmotic device for the controlled and continuous delivery of a drug wherein the device comprises: a) a core containing a drug and an osmotic agent; b) a semipermeable laminate, surrounding the core, which includes an external semipermeable lamina and an internal semipermeable lamina; and c) a passageway which communicates the core with the exterior of the device. The two semipermeable laminae maintain their chemical and physical integrity in the presence of the drug and fluid from the environment. The passageway of Theeuwes et al. '334 includes a passageway, orifice or bore through the laminate formed by mechanical procedures, or by eroding an erodible element, such as a gelatin plug, in the environment of use. Theeuwes et al. '334 does not disclose an osmotic device which membrane ruptures even though it has a preformed aperture in the membrane.

U.S. Pat. No. 4,576,604 to Guittard et al. ("Guittard et al. '604") corresponds to Argentina Patent No. 234,493 and discloses several different embodiments of an osmotic device having a drug in the core and at least one lamina surrounding the core. Specifically, one embodiment of the osmotic device comprises: a) a core containing a drug formulation which can include an osmotic agent for controlled release of the drug; b) a semipermeable wall comprising an inner semipermeable lamina, a middle microporous lamina, and an outer water soluble lamina containing drug; and c) a passageway which communicates the core with the exterior of the device. Guittard et al. '604 does not disclose an osmotic device which membrane ruptures even though it has a preformed aperture in the membrane.

U.S. Pat. No. 4,673,405 to Guittard et al. ("Guittard et al. '405") discloses an osmotic device comprising: a) a core, or compartment, containing a beneficial agent; b) an inert semipermeable wall containing a beneficial agent surrounding the core; and c) at least one passageway in the wall of the osmotic device which is formed when the osmotic device is in the fluid environment of use and the fluid contacts and thus releases the beneficial agent in the wall, wherein the formed passageway communicates with the compartment in the osmotic device and the exterior of the device for dispersing the beneficial agent from the compartment when the device is in the fluid environment of use. Guittard et al. '405 discloses the use of an erodible element to form the passageway; however, it does not disclose an osmotic device which membrane ruptures even though it has a preformed aperture in the membrane.

U.S. Pat. No. 5,558,879 to Chen et al. ("Chen et al. '879") discloses a controlled release tablet for water soluble drugs in which a passageway is formed in the environment of use, i.e., the GI tract of a person receiving the formulation. Specifically, the controlled release tablet consists essentially of: a) a core containing a drug, 5-20% by weight of a water soluble osmotic agent, a water soluble polymer binder and a pharmaceutical carrier; and b) a dual layer membrane coating around the core consisting essentially of: (1) an inner sustained release coating containing a plasticized water insoluble polymer and a water soluble polymer; and (2) an outer immediate release coating containing a drug and a water soluble polymer. Although Chen et al '879 discloses the formation of a passageway in a controlled release tablet in an environment of use to form an osmotic tablet. Chen et al. do not disclose a coated controlled release device which membrane ruptures even though it has a preformed aperture in the membrane.

U.S. Pat. No. 4,810,502 to Ayer et al. ("Ayer et al. '502") discloses an osmotic dosage form for delivering pseudoephedrine (Ps) and brompheniramine (Br) which comprises: a) a core containing Ps and Br; b) a wall surrounding the core comprising cellulose acylate and hydroxypropylcellulose; c) a passageway in the wall for delivering the drug; and d) a lamina on the outside of the wall comprising Ps, Br, at least one of hydroxypropylcellulose and hydroxypropyl methylcellulose, and poly(ethylene oxide) for enhancing the mechanical integrity and pharmacokinetics of the wall. Ayer et al. '502 does not disclose a coated controlled release device which membrane ruptures even though it has a preformed aperture in the membrane.

U.S. Pat. No. 4,801,461 to Hamel et al. ("Hamel et al. '461") discloses an osmotic dosage form for delivering pseudoephedrine (Ps). Specifically, the osmotic dosage form comprises: a) a core containing varying amounts of Ps; b) a semipermeable wall surrounding the core comprising varying amounts of cellulose acetate or cellulose triacetate and varying amounts of hydroxypropylcellulose; c) a passageway in the wall for delivering the drug from the core; and optionally d) a lamina on the outside of the wall comprising Ps. The core can also contain one or more of sodium chloride, microcrystalline cellulose, hydroxypropyl methylcellulose, magnesium stearate, and poly(vinylpyrrolidone). The passageway of this device can extend through the semipermeable wall alone or through both the semipermeable wall and the outer lamina. The passageway also includes materials that erode or leach in the environment of use. A variety of erodible materials are listed as suitable for use in forming the passageway. Hamel et al. '461 does not, however, disclose a coated controlled release device which membrane ruptures even though it has a preformed aperture in the membrane.

U.S. Pat. No. 5,681,584 to Savastano et al. ("Savastano et al. '584") discloses a controlled release drug delivery device comprising: a) a core containing a drug, an optional osmotic agent and optional excipients; b) a delayed release jacket comprising at least one of a binder, an osmotic agent and a lubricant surrounding the core; c) a semipermeable membrane surrounding the delayed release jacket and optionally having a passageway; d) a drug-containing layer either on the outside of the semipermeable membrane or between the semipermeable membrane and the delayed release jacket; and e) an optional enteric coat either on the outside of the drug-containing layer, between the drug-containing layer and the semipermeable membrane or on the outside of the semipermeable membrane when the drug-containing layer is between the delayed release jacket and the semipermeable membrane. Thus, the device of Savastano et al. '584 does not rupture even though it has a preformed passageway.

U.S. Pat. No. 6,004,582 to Faour et al. (Faour et al. '582) discloses a multi-layered osmotic device comprising a core surrounded by a semipermeable membrane having a preformed hole in it. The hole is subsequently plugged by an inert erodible water soluble coating and then covered with a water soluble drug-containing coating. This patent does not disclose a coated controlled release device which membrane ruptures even though it has a preformed aperture in the membrane.

U.S. Pat. No. 5,873,793 to Emerton et al. (Emerton et al. '793) and U.S. Pat. No. 5,376,771 to Roy (Roy '771) disclose laser apparatuses capable of simultaneously forming a plurality of holes on the semipermeable membrane of an osmotic device. These patents do not disclose a coated controlled release device which membrane ruptures even though it has a preformed aperture in the membrane.

Additional exemplary osmotic devices for the controlled delivery of active agents are described in U.S. Pat. No. 3,845,770 and Argentina Patent No. 199,301 which disclose an osmotic device formed by a wall that surrounds a compartment-housing agent. The wall has a passageway or orifice that links the compartment to the environment of use. The wall is made of semipermeable material that is semipermeable to an external fluid and impermeable to an active agent within the device. Neither of these patents discloses a coated controlled release device which membrane ruptures even though it has a preformed aperture in the membrane.

U.S. Pregrant Patent Publication No. 2002/0099361 to Faour discloses an osmotic device having a preformed passageway that increases in size during use by rupture of the membrane surrounding the preformed passageway. The membrane is optionally etched to promote rupture of the membrane along a predetermined path and/or to a predetermined extent. The '361 publication does not disclose a coated controlled release device which membrane ruptures at a location spaced apart from or away from the preformed aperture in the membrane. The '361 publication only discloses rupture of the membrane on the edge defining the preformed passageway in the membrane.

While the prior art discloses a wide variety of release mechanisms used in osmotic devices and coated controlled release devices, no single release mechanism provides a coated controlled release dosage form comprising a preformed passageway wherein the coating of the dosage form ruptures at a location spaced away from the preformed passageway during use of the device so that controlled delivery of all or substantially all the amount of active agent is provided or so that the rate of release of the drug increases over time.

SUMMARY OF THE INVENTION

A method of making such an osmotic device has now been discovered. The present osmotic device overcomes many of the disadvantages inherent in related prior art osmotic devices because it is capable of providing approximately complete delivery of the active substance contained in the core and an increased release rate of active substance during use, and it enables release of large particle size and/or generally insoluble active agents.

The present invention overcomes some of the disadvantage of the prior art by providing a coated controlled release device, wherein a coating surrounding the core of the device ruptures during use even though the coating has a preformed passageway, thereby allowing controlled delivery of an active substance contained in the core of the device to an environment of use. The present invention also provides a method for making an osmotic device having a membrane that ruptures at a location away from a preformed passageway in the membrane. The benefits provided by the present invention include: 1) approximately complete delivery of the active substance contained in the core; 2) an increased release rate of active substance during use as the second passageway permits additional contents of the core to be released more quickly than would occur through just the preformed passageway alone; and 3) enablement of the release of large particle size and/or generally insoluble active agents.

One aspect of the present invention provides a controlled release device for the controlled delivery of approximately all of an active substance contained in the core of the device, wherein the device comprises: a) a core comprising an active agent, such as nifedipine, at least one osmopolymer, and at least one excipient; b) a semipermeable membrane surrounding the core; c) a preformed passageway in the semipermeable membrane for release of the contents of the core, wherein the membrane ruptures during use of the osmotic device to form a spaced away second aperture such that the device provides an increased release rate of active agent during use as compared to a control osmotic device which membrane does not rupture, and the passageways together provide a controlled release of the contents of the core. The preformed passageway does not connect with the passageway formed in situ (in the environment of use) by rupture, meaning that the second passageway, after being formed, remains spaced away from the preformed passageway.

Specific embodiments of the invention include those embodiments wherein: a) at least 80% of the active agent is released by the end of use; b) at least 90% of the active agent is released by the end of use; c) the second passageway is smaller than or approximates the size of the preformed passageway; d) the second passageway is larger than the preformed passageway; e) the membrane comprises a weakened section wherein the second passageway is formed; f) the preformed passageway expands in size by rupture (dissolution or breakage) of the membrane; g) the second passageway forms at a predetermined location of the membrane; h) the core contains a swellable material; i) the core comprises a nucleus that is coated with active agent and at least one excipient; j) the exterior of the semipermeable membrane has at least one coating that effects the operation of the osmotic device in a manner according to the properties of the coating; and/or k) the second passageway forms due to an increase of internal osmotic pressure of the core during use of the device.

One aspect of the present invention provides a method of preparing the osmotic device, wherein a core comprising an active agent and at least one excipient is covered with a semipermeable membrane that is perforated to form at least one preformed passageway, and the membrane is adapted to rupture and form a different second passageway during use of the osmotic device. In this aspect, the invention provides a method of preparing a coated controlled release device comprising at least two different passageway, the method comprising the steps of: a) preparing a coated controlled release device comprising a core, a wall surrounding the core, and a preformed passageway in the wall; and b) exposing the device to an environment of use whereby the wall ruptures at a location spaced away from the preformed passageway to form a second passageway in the wall. An active agent included in the core is released at a controlled rate (over an extended period of time) first from the preformed passageway and then from both passageways after the second passageway is formed.

Other aspects of the invention provide a method of making a coated controlled release device wherein a passageway is formed by other mechanical means; by variations in the viscosity, the molecular weight, or the degree of substitution of the at least one excipient; by the use of plasticizers in the semipermeable membrane; or by the use of a brittling agent in a wall of the device.

The present invention further provides a method for treating a symptom, disorder and/or disease by the administration of at least one coated controlled release device to a subject, the device comprising a core substantially enclosed within a wall comprising a preformed passageway, wherein the wall is adapted to rupture during use of the device to form a second passageway at a region spaced away from the preformed passageway such that an active agent in the core is released during use over an extended period of time through the passageways.

Other specific embodiments of the invention include those wherein: 1) the second passageway is formed more than about one hour after exposure of the device to an environment of use; 2) the second passageway is formed in less than about one hour after exposure of the device to an environment of use; 3) the second passageway is formed more than about three hours after exposure of the device to an environment of use.

Different environments for use of the device include biological environments such as the oral, ocular, nasal, vaginal, glands, gastrointestinal tract, rectum, cervical, intrauterine, arterial, venous, otic, sublingual, dermal, epidermal, subdermal, implant, buccal, bioadhesive, mucosal and other similar environments. Likewise, it may be used in aquariums, industrial warehouses, laboratory facilities, hospitals, chemical reactions and other facilities.

Other features, advantages and embodiments of the invention will become apparent to those skilled in the art by the following description, accompanying examples and appended claims.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Figure 1:
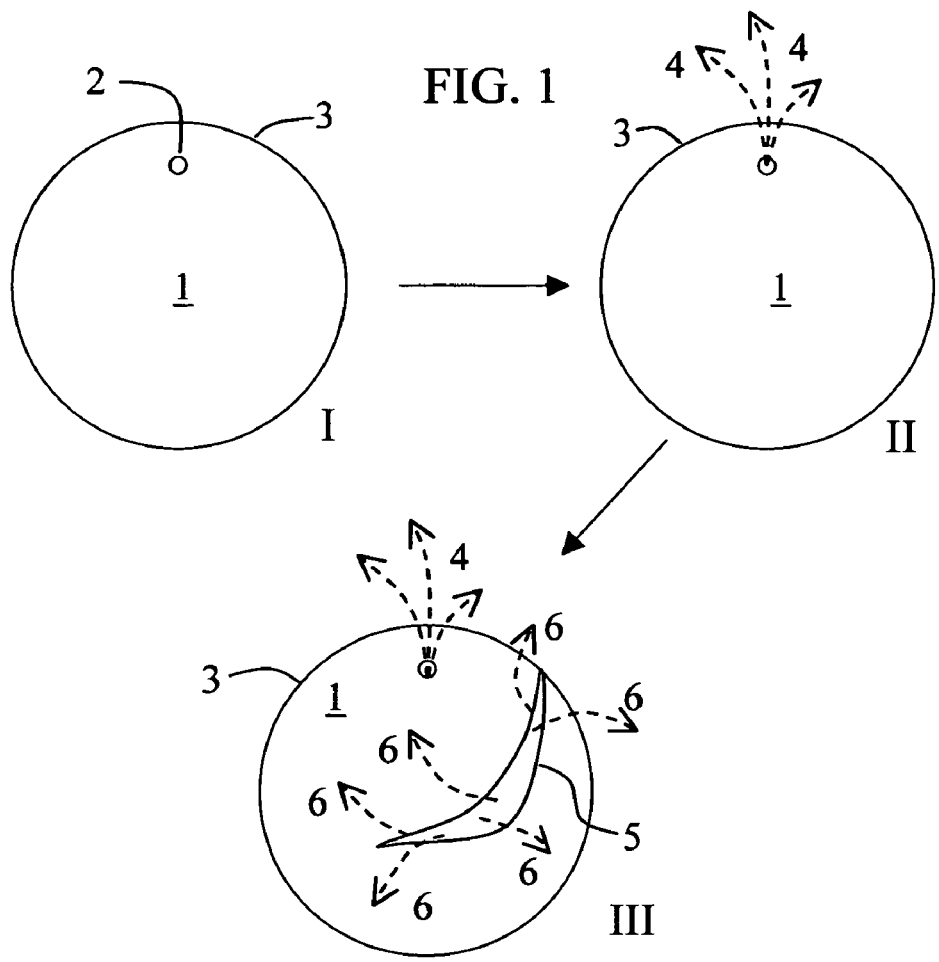
FIG. 1 depicts three general stages (I-III) of operation of a controlled release device according to Example 1.

By "immediate release" is meant a release of an active agent to an environment over a period of seconds to no more than about 30 minutes once release has begun and release begins within a second to no more than about 15 minutes after administration.

By "rapid release" is meant a release of an active agent to an environment over a period of 1-59 minutes or 1 minute to three hours once release has begun and release can begin within a few minutes after administration or after expiration of a delay period (lag time) after administration.

By "controlled release" is meant a release of an active agent to an environment over a period of about eight hours up to about 12 hours, 16 hours, 18 hours, 20 hours, a day, or more than a day. A controlled release device can be a sustained release or extended release device. By "sustained release" is meant a controlled release of an active agent to maintain a constant drug level in the blood or target tissue of a subject to which the device is administered. By "extended release" is meant a controlled release of an active agent from a dosage form to an environment over an extended period of time. A controlled release device generally effects at least a two-fold reduction in dosing frequency as compared to the drug presented in a conventional dosage form (e.g., a solution or rapid releasing conventional solid dosage forms).

The terms "osmotic device" and controlled release device are generally used herein interchangeably; however, an osmotic device is considered one embodiment of the many types of controlled release devices covered by the present invention. A controlled release device comprises a core surrounded by a wall that permits release of one or more drugs through a preformed passageway in the wall. The wall comprises one or more lamina selected from one or more coatings and/or one or more membranes, wherein each of the coatings or membranes is inert or comprises one or more drugs. In other words, a wall is a single-layered wall (one lamina) or a multi-layered (two or more laminas) wall. During use, the wall, or at least one lamina of the wall, maintains its physical integrity during the period of delivery of drug from the core of the device. The preformed passageway and the second passageway (the one formed during use of the device) must pass through the one or more lamina(s) of the wall that maintains its physical integrity. It is only necessary that at least one of the layers (laminas) of the wall retain its physical integrity during the period of delivery of the active agent and that the preformed passageway and second passageway occur in the same lamina.

An osmotic device is a controlled release device wherein the wall comprises a semipermeable membrane surrounding the drug-containing core, and optionally one or more other coatings and/or membranes. The preformed passageway is disposed at least through the semipermeable membrane.

The coating(s) or membrane(s) of the wall can be applied by compression or by spraying. A controlled release device can comprise a combination of laminas wherein each is independently applied by compression or spraying. A multi-layered wall can comprise: 1) one or more compression coatings and one or more sprayed-on coatings; 2) one or more compression coatings and one or more sprayed-on membranes; 3) two or more sprayed-on membranes; 4) two or more sprayed-on coatings; or 5) two or more compression coatings.

FIG. 1 depicts three general stages (I-III) of operation of a controlled release device (1) according to Example 1. The device comprises a core surrounded by a wall (3) which includes a preformed passageway (2). Stage I, which occurs prior to through to a first period of time after administration, includes no or substantially no release of drug from the core through the preformed passageway. During the first period, the device is exposed to an environment of use. For example, an osmotic device comprising an active agent is administered orally to a subject. Drug or core composition release (4) through the preformed passageway begins during Stage II such that drug is released at a controlled rate over an extended period of time. The internal osmotic pressure of the device builds up during Stage II. After expiration of a second period of time, the internal osmotic pressure has built up sufficiently to cause rupture of the wall (3) at a region spaced away from the preformed passageway thereby forming a second passageway in the wall (Stage III). The composition in the core is then released through at least both passageways.

Without being held bound to a particular mechanism of operation, it is believed that the osmotic device of the invention delivers one or more active agents to an environment of use as follows. Referring to FIG. 1, the osmotic device (1) comprises a core containing an active agent, an osmopolymer, an osmagent and at least one excipient. The core is surrounded by a semipermeable membrane (3) having a preformed passageway (2) that delivers the active agent to an environment of use in a controlled manner for a first period of time. Following sufficient build-up of the internal osmotic pressure of the device, the wall ruptures to form the second passageway. Rupture of the wall can be due to excessive internal osmotic pressure buildup in combination with an undersized preformed passageway and/or a thin, weak or brittle wall. For example, a core exhibiting a high osmotic pressure during use can be used in combination with a small preformed passageway having an optional scored region spaced away from the preformed passageway. By making the semipermeable membrane thin, weak or brittle, it will rupture in a region spaced away from the preformed passageway to form a second passageway, thereby effecting an increase in the combined total surface area of the passageways. Increasing the surface area of the passageway results in an increased rate of release of the composition from the core.

Figure 2:
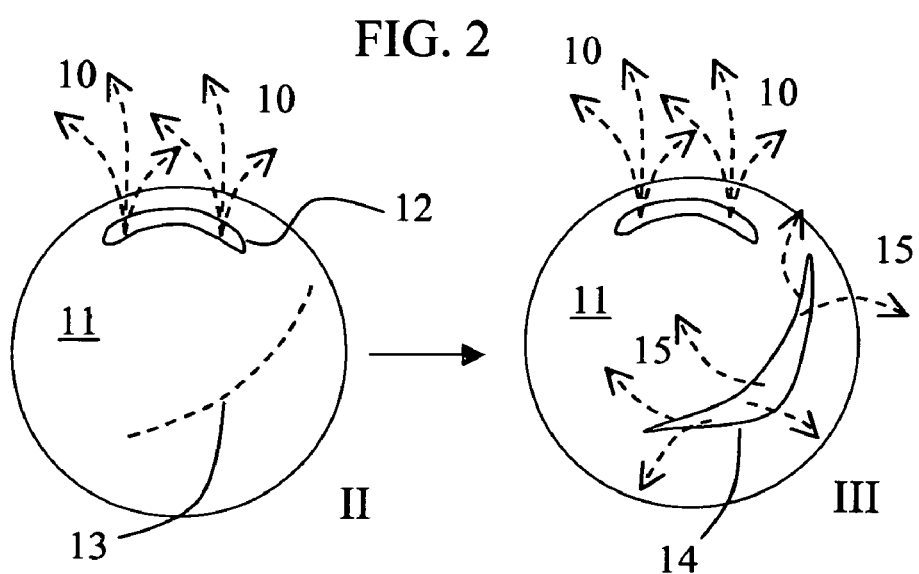
FIG. 2 depicts two general stages (II-III) of operation of a controlled release device according to Example 2.

FIG. 2 depicts two general stages (II-III) of operation of a controlled release device according to Example 2. In this embodiment, a controlled release device (11) comprises a slot-shaped preformed passageway (12) in the coat. An etched region (13) spaced away from the preformed passageway. Stage II depicts release of the core ingredients through the slot during use of the device. The wall then ruptures along the etching resulting in Stage III to form a second passageway (14) through which the core contents are released (15).

Figure 6:
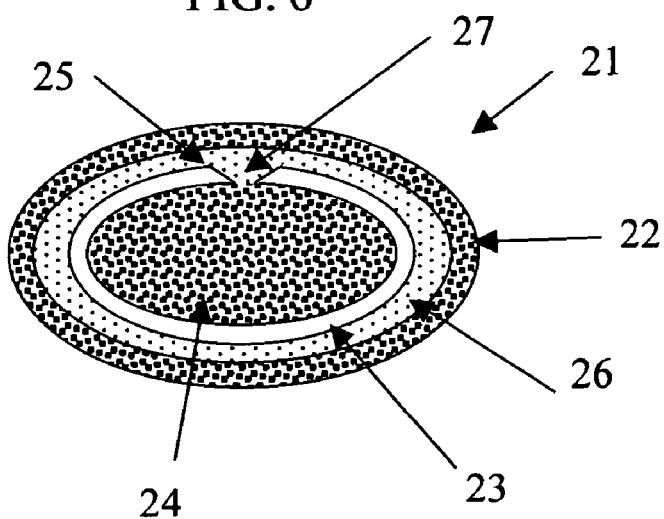
FIG. 6 depicts a sectional side view of a multi-layered controlled release device according to the invention.

When used as a drug delivery device, the osmotic device of the invention can operate as follows provided the right combination of materials is used to formulate the various coatings, the membrane and the core of the osmotic device. FIG. 6 illustrates an embodiment of the invention wherein a polymer coat (26) has been added to form a plug (27) in the preformed passageway (25). In this embodiment, the core has been coated with a semipermeable membrane, which was then perforated by mechanical means, such as a laser, to form the preformed passageway (25). The inert water soluble polymer coat (26) was then applied to the semipermeable membrane (23) to form the plug (27). The external coat (22), which may contain an optional second active agent, was then applied to the polymer coat (26). Following administration to a mammal, the acid soluble, erodible and/or swellable external coat (22) begins to dissolve, erode, swell and/or detach from the osmotic device thereby releasing any second active agent contained therein into the stomach. As the osmotic device (21) moves through the GI tract, portions of the external coat (22) will have partially or completely dissolved, eroded or become detached, thereby exposing the polymer coat (26), which in some embodiments is not soluble in acidic gastric juices. The polymer coat (26) then dissolves or erodes in one or more regions of the intestines according to the particular materials that comprise the polymer coat (26). For example, materials that are soluble in fluids having a pH of 4-6 will dissolve in the small intestine, whereas materials that dissolve in fluids having a pH of 7-8 will dissolve in the large intestine or colon. Combinations of these materials can be used. The polymer coat (26) can also be microporous to permit absorption of water into the core (24) of the osmotic device (21) without dissolution of the polymer coat (26). Once the polymer coat (26) has dissolved or eroded or once at least the plug (27) of the polymer coat (26) has dissolved or eroded, the core (24) will begin to release the first active agent through the passageway (25) into the intestines. The various coatings surrounding the semipermeable membrane can be compression coatings or sprayed-on coatings.

Even though the first active agent is released through the passageway (25), the internal osmotic pressure of the device continues to increase until the semipermeable membrane ruptures at a location away from the preformed passageway (25) to form a second passageway. The preformed passageway and/or the second passageway can optionally increase from its initial size to a larger second size. If one of the passageways expands in size, it does so over time regardless of the plug (27) formed by the polymeric coat (26) that blocks all or part of the passageway (25). The increase in size of the passageway can be 10%, 25%, 50%, 75%, 100%, or more, depending upon the materials used to form the semipermeable membrane and the core.

Figure 7:
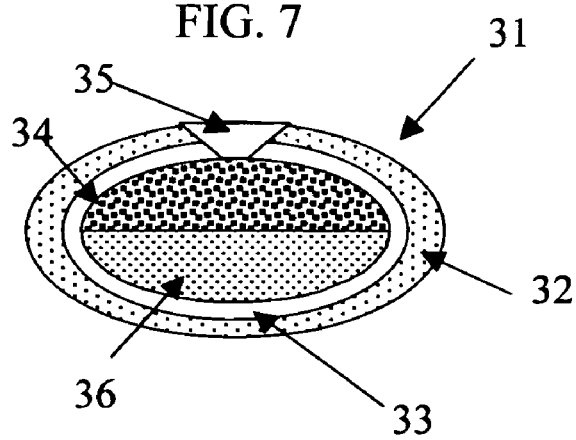
FIG. 7 depicts a sectional side view of a conventional push-pull controlled release device according to the invention.

In the embodiment of FIG. 7, the active agent or an osmotic agent will dissolve or swell in the fluid that enters into the core (34, 36) through the semipermeable membrane (33) thereby creating an osmotic pressure gradient across the membrane, which gradient provides the force required to push the active agent through the passageway from the core to the exterior of the osmotic device (31). The exemplary core comprises a drug-containing first composition (34) and a water swellable second composition (36). As water permeates the second composition it swells and expands in size thereby forcing the first composition through the passageways. The active agent will continue to be released from the core until osmotic equilibrium is reached between the core and the environment of use. This equilibration of osmotic forces occurs gradually over a period of time thereby serving to control the release of and thus the release profile for the active agent. The release of the active agent slows as osmotic equilibrium is approached, and then stops when osmotic equilibrium is reached. The extent to which the release of the active agent is controlled is known to depend upon a number of other variables such as the permeability of the semipermeable membrane and the magnitude of the osmotic pressure gradient.

In the embodiment of FIG. 7, the preformed passageway (33) extends from the core through to the exterior of the device, since the preformed passageway was formed after the external coat (32) was applied. The osmotic device can provide a release rate of active agent that increases during use. The active agents in the core and external coat can be the same or different.

Figure 3:
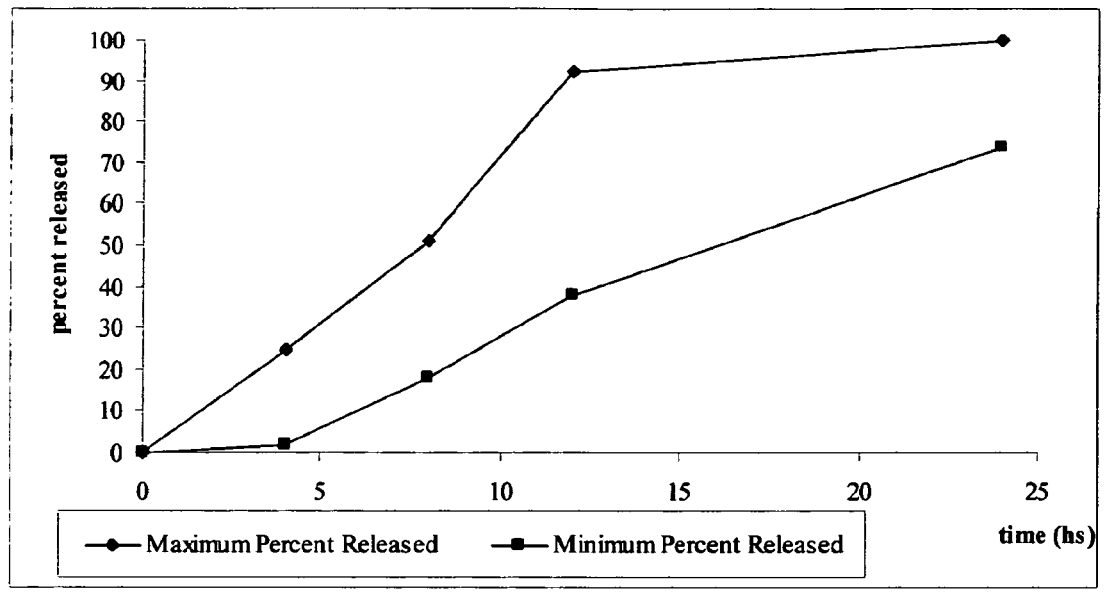
FIG. 3 depicts the maximum and the minimum percentage of nifedipine released from several samples of the osmotic device according to Example 1.

It is believed that the osmotic device of the invention produces release profiles as herein described. FIG. 3 depicts the average (from several samples) maximum and the average (from several samples) minimum percentage of nifedipine released of the osmotic device according to Example 1. The release profile for the core of a controlled release device of the invention generally resembles a sigmoidal release profile indicating that drug release occurs at a first rate, then it accelerates to a second rate and finally tapers off (slows down) to a third rate.

The release profile of the osmotic device of the invention may vary from that shown in FIG. 3 according to the materials used to form the core and the semipermeable covering the core, as well as the method used to form the passageway. For example, the release profile can be influenced by the various alternate embodiments of the preformed aperture such as the different sizes, shapes and functions depicted in FIG. 5. The release profile can also be influenced by the amount of nifedipine used to form the core, the amount of excipient used to form the core, the type of excipient used to form the core, and the amount or type of any other materials used to form the core such as osmotically effective solutes, osmotic agents, osmopolymers, or osmagents. The release profile can also be influenced by the material used to form the wall, e.g., membrane, covering the core or by the material used to form any coating on the wall. The release profile can also be influenced by when the second passageway forms relative to initial exposure of the device as well as by the size of the second passageway once it forms. The device of the invention may also have a release profile that generally resembles a first order or pseudo first order release profile.

As depicted in FIG. 3, the release profile is generally described as follows:

| Time (h) | Maximum Percent Released | Minimum Percent Released |
|---|---|---|
| 4 | 25 | 2 |
| 8 | 51 | 18 |
| 12 | 92 | 38 |
| 24 | 100 | 74 |

The values set forth in the above table are approximate numbers. Depending upon the conditions of measurement as well as the assay used to determine those values, they may have a standard deviation of ±5% or ±10% of the indicated value.

Figure 4:
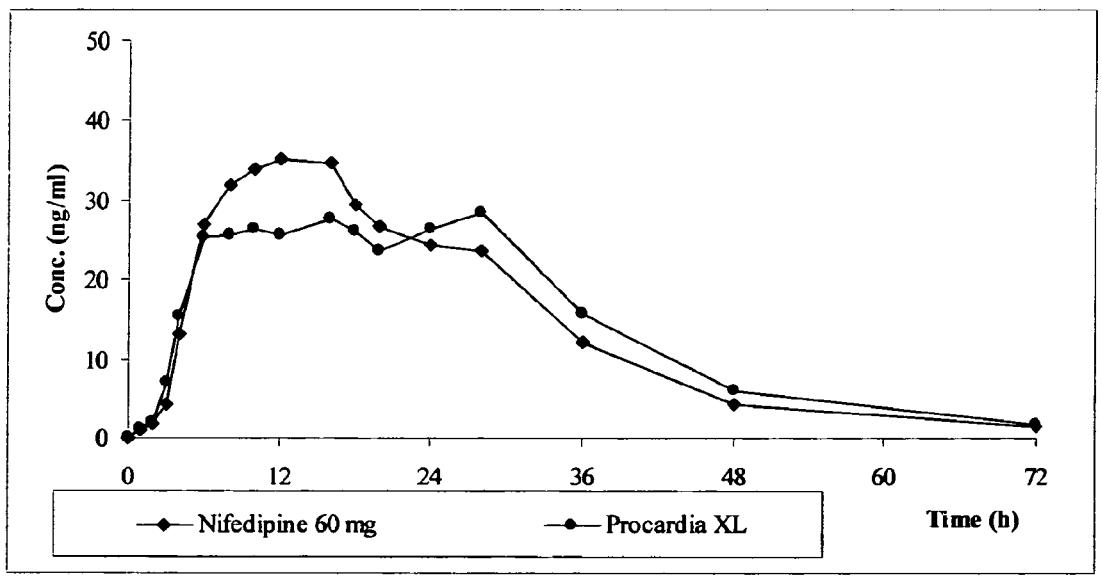
FIG. 4 depicts the mean plasma profile for 24 healthy male subjects to which a nifedipine 60 mg tablet of Example 1 and a Procardia® XL 60 mg tablet as the reference treatment were administered in an open-label, single dose, 2×2 cross over pharmacokinetic study.

FIG. 4 depicts the mean plasma profile for 24 healthy male subjects to which the nifedipine 60 mg tablets of Example 1 and Procardia® XL 60 mg as the reference treatment were administered in an open-label, single dose, 2×2 cross over pharmacokinetic study, as described in Example 5. The average bioequivalence was evaluated by calculating the 90% classical confidence interval for the main PK parameters peak concentration and area under the curve as shown in the following table.

| Parameter | Geometric LSM | | Ratio | 90% Classic CI | |
|---|---|---|---|---|---|
| | Test | Ref | % Ref | Lower | Upper |
| Cmax ng/ml | 40.4 | 36.5 | 110.6 | 98.8 | 123.8 |
| AUCt ng/(ml * h) | 917.6 | 895.7 | 102.5 | 87.2 | 120.4 |
| AUCinf ng/(ml * h) | 960.4 | 935.6 | 102.7 | 88.0 | 119.8 |

There was no statistically significant difference between the formulations with regards to major pharmacokinetic parameters by ANOVA. The 90% confidence intervals for the geometric mean test-to-reference area under the curve and peak concentration ratios were within the bioequivalence interval 0.80-1.25. The nifedipine 60 mg tablets described in Example 1 were bioequivalent to Procardia® XL 60 mg in terms of pharmacokinetics.

The nifedipine 60 mg tablets described in Example 1 provided therapeutically effective levels of nifedipine between the period of about 1 to about 30 hours after administration. Therapeutic nifedipine plasma concentration levels ranged from about 10 to about 100 ng/ml. The mean $C_{max}$ was 40.4 ng of nifedipine per ml of plasma at about 13 hours after administration, as shown in FIG. 3.

Although the figures depict the controlled release device (1) configured as an oval or circular pill or tablet, it should be understood that the device can assume any shape or form currently known in the art of osmotic devices. That is, the device may assume any different shape and/or size according to which are optimal for the intended environment of use. In particular embodiments, the shape and size of the device will be optimal for use in mammal such as animals or human beings. The device of the invention can be a pill, sphere, tablet, bar, plate, granule, agglomerate or others known to those of ordinary skill. The osmotic device can also include surface markings, cuttings, grooves, letters and/or numerals for the purposes of decoration, identification and/or other purposes.

When a soluble plug (27) temporarily blocks all or a part of the preformed passageway prior to use of the osmotic device (see FIG. 6), the polymeric coat (26) covering the semipermeable membrane (23) and blocking the passageway (25) is made of synthetic, semisynthetic or natural material which, through selective dissolution and/or erosion shall allow the passageway to be unblocked thus allowing the process of osmotic delivery to start. This slow or fast dissolving polymer coat (26) can be impermeable to a first external fluid, while being soluble in a second external fluid. This property can help to achieve a controlled and selective release of the active compound in the nucleus.

The polymer coat (26) will generally comprise an inert and non-toxic material which is at least partially, and generally substantially completely, soluble and/or erodible in an environment of use. The polymer coat (26) can be soluble in one or more environments of use. For example, the polymer coat (26) can be soluble in the same environment of use in which the external coat (22) is soluble in, or it can be soluble in the same environment of use in which the core (25) is soluble. Although the art discloses microporous layers comprising materials which can be included in the polymer coat (26), the presence of poly(vinylpyrrolidone)-(vinyl acetate) copolymer in the polymer coat (26) has been found to provide advantageous properties and characteristics to the polymer coat. Thus, the polymer coat (26) will, in some embodiments, comprise poly(vinylpyrrolidone)-(vinyl acetate) copolymer, and it can also include other water soluble materials useful for this type of coat. Exemplary materials are disclosed in U.S. Pat. Nos. 4,576,604 and 4,673,405, and the text Pharmaceutical Dosage Forms: Tablets Volume 1, Second Edition. A. Lieberman. ed. 1989, Marcel Dekker, Inc. the relevant disclosures of which are hereby incorporated by reference.

In specific embodiments, the polymer coat (26) will be insoluble in the fluid of a first environment of use, such as gastric juices, acidic fluids, or polar liquids, and soluble or erodible in the fluid of a second environment of use, such as intestinal juices, substantially pH neutral or basic fluids, or apolar liquids. A wide variety of other polymeric materials are known to possess these various solubility properties and can be included in the polymer coat (26). Such other polymeric materials include, by way of example and without limitation, cellulose acetate phthalate (CAP), cellulose acetate trimelletate (CAT), poly(vinyl acetate) phthalate (PVAP), hydroxypropyl methylcellulose phthalate (HPMCP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, Eudragit L-30-D™ (MA-EA, 1:1), Eudragit L-100-55™ (MA-EA, 1:1), hydroxypropyl methylcellulose acetate succinate (HPMCAS), Coateric™ (PVAP), Aquateric™ (CAP), AQUACOAT™ (HPMCAS) and combinations thereof. The polymer coat (26) can also comprise dissolution aids, stability modifiers, and bioabsorption enhancers.

When the polymer coat (26) is intended to be dissolved, eroded or become detached from the core in the colon, materials such as hydroxypropylcellulose, microcrystalline cellulose (MCC, Avicel™ from FMC Corp.), poly (ethylene-vinyl acetate) (60:40) copolymer (EVAC from Aldrich Chemical Co.), 2-hydroxyethylmethacrylate (HEMA), MMA, terpolymers of HEMA:MMA:MA synthesized in the presence of N,N'-bis(methacryloyloxyethyloxycarbonylamino)-azobenzene, azopolymers, enteric coated timed release system (Time Clock® from Pharmaceutical Profiles, Ltd., UK) and calcium pectinate can be included in the polymer coat (26).

One polymeric material for use in the polymer coat (26) involves enteric materials that resist the action of gastric fluid avoiding permeation through the semipermeable wall while one or more of the materials in the core (25) are solubilized in the intestinal tract thereby allowing delivery of a drug in the core (25) by osmotic pumping to begin. A material that easily adapts to this kind of requirement is a poly(vinylpyrrolidone)-vinyl acetate copolymer, such as the material supplied by BASF under its Kollidon VA64 trademark, mixed with magnesium stearate and other similar excipients. The polymer coat (26) can also comprise povidone, which is supplied by BASF under its Kollidon K 30 trademark, and hydroxypropyl methylcellulose, which is supplied by Dow under its Methocel E-15 trademark. The materials can be prepared in solutions having different concentrations of polymer according to the desired solution viscosity. For example, a 10% P/V aqueous solution of Kollidon K 30 has a viscosity of about 5.5-8.5 cps at 20° C., and a 2% P/V aqueous solution of Methocel E-15 has a viscosity of about 13-18 cps at 20° C.

The polymer coat can also comprise other materials suitable which are substantially resistant to gastric juices and which will promote either enteric or colonic release. For this purpose, the polymer coat can comprise one or more materials that do not dissolve, disintegrate, or change their structural integrity in the stomach and during the period of time that the osmotic device resides in the stomach. Representative materials that keep their integrity in the stomach can comprise a member selected from the group consisting of (a) keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkylacrylic acid and alkylacrylic acid alkyl esters, acrylic resins such as dimethylaminoethylmethacrylate-butylmethacrylate-methylmethacrylate copolymer of 150,000 molecular weight, methacrylic acid-methylmethacrylate 50:50 copolymer of 135,000 molecular weight, methacrylic acid-methylmethacrylate-30:70-copolymer of 135,000 mol. wt., methacrylic acid-dimethylaminoethyl-methacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

As used herein, the term "preformed passageway" refers to a passageway or passageway precursor that has been formed on the wall of the device by mechanical means, such as by a laser, drill and/or etching apparatus. A preformed passageway is optionally plugged after initial formation, such as depicted in FIG. 6. If a water soluble plug is used, the preformed passageway will increase in size even after all of the plug has been removed from the preformed passageway. The term "preformed passageway" is not intended to cover pores, holes, apertures, channels or other similar structures formed in the semipermeable membrane by incorporation of pore formers, water soluble particulates, or similar materials known to those of ordinary skill, into the wall of the coated controlled release device, e.g. the semipermeable membrane during manufacture of the osmotic device. The invention does include, however, a controlled release device having a preformed passageway and one or more other pores, holes apertures, channels or other similar structures known to those of ordinary skill.

In an alternate embodiment, plasticizers can be included in the present device to create additional passageways or to aid in forming the second passageway in a respective coating or wall or membrane, and/or to modify the properties and characteristics of the polymers used in the coats or core of the device. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in *Poly(ethylene glycol) Chemistry: Biotechnical and Biomedical Applications* (J. M. Harris, Ed.; Plenum Press, NY) the disclosure of which is hereby incorporated by reference.

The wall or semipermeable membrane can also comprise a flux enhancing agent. The flux enhancing agent increase the volume of fluid imbibed into the core. The flux enhancing agents are water-soluble components such as sodium chloride, potassium chloride, sugar, sucrose, sorbitol, mannitol, polyethylene glycol (weight av. molecular weight 380-3700), propylene glycol, hydroxypropyl cellulose, hydroxypropyl methylcellulose and mixtures thereof. In other embodiment the wall also provides the release of drug from the core through pores. The porosity of the wall will vary according to its composition. Preferred copolymers used in the manufacturing of the wall include: poly(ammonium methacrylate) copolymer RL (Eudragit™ RL), poly(ammonium methacrylate) copolymer (type A-USP/NF), poly(aminoalkyl methacrylate) copolymer RL-JSP I), and (ethyl acrylate)-(methyl methacrylate)-[(trimethylammonium)-ethylmethacrylate] (1:2:0.2) copolymer, MW 150,000. More preferred polymers include (Röhm Pharma, Weiterstadt): Eudragit™ RS 100: solid polymer, Eudragit™ RL 12.5: 12.5% solution in solvent, Eudragit™ RL 30 D: 30% aqueous dispersion, and other equivalent products.

The following poly (ammonium methacrylate) copolymers can also be used: ammonium methacrylate copolymer RS (Eudragit™ RS), poly(ammonium methacrylate) copolymer (type B-USP/NF), poly(aminoalkyl methacrylate) copolymer (RSL-JSP I), (ethyl acrylate)-(methyl methacrylate)-[(trimethylammonium)-ethyl methacrylate] (1:2:0.1) copolymer, PM 150,000. Specific polymers include (Röhm Pharma, Weiterstadt): Eudragit™ RS 100: solid polymer, Eudragit™ RS 12.5: 12.5% solution in solvent, Eudragit™ RS 30 D: 30% aqueous dispersion and other equivalent products.

An alternative embodiment of the invention includes pore former(s) in the wall to form additional passageways over time. Acceptable pore formers include polysaccharides such as mannitol, galactose, mannose, aldohexose, altrose, talose and sorbitol; alkali metal salts such as sodium chloride, lithium carbonate, potassium chloride, and potassium sulfate; alkaline earth metal salts such as calcium phosphate, and calcium nitrate; and transition metal salts such as zinc sulfate, ferric chloride, and ferrous sulfate.

The controlled release device will deliver one or more active agents from the core and/or from the external coating, in a controlled manner, and mechanisms employed for such controlled delivery can include active agent release that is pH-dependent or pH-independent; diffusion or dissolution controlled; pseudo-zero order (approximates zero-order release), zero-order, pseudo-first order (approximates first-order release), or first-order; or rapid, slow, delayed, timed or sustained release or otherwise controlled release. The release profile for the active agent can also be sigmoidal in shape, wherein the release profile comprise an initial slow release rate, followed by a middle faster release rate and a final slow release rate of active agent.

Release of active agent from the core can be delayed such that the release profile of active agent will exhibit delayed and then controlled release. Release of active agent from the external coat can also be delayed such that the release profile of active agent will exhibit delayed and then immediate or controlled release.

The external coat is comprised of one or more coatings, which are generally independently selected at each occurrence from the group consisting of: a drug-containing coating, a release rate modifying coating, a porous coating; a soluble coating, an insoluble coating, a semipermeable membrane; and a delayed release coating. A delayed release coating can be a timed-release coating, enteric coating, colonic delivery coating, gastric fluid resistant coating or other such coating used in the pharmaceutical sciences for delaying the release of a compound from a dosage form for a period time after exposure to an environment of use.

In an alternate embodiment, the external coat may contain a second active agent that may or may not be the same as a first active agent in the core. Depending on the composition of the external coat, the second active agent is available for immediate, slow, delayed, sustained, pseudo-first order, pseudo-zero order, timed, controlled release or combinations thereof. The second active agent can be applied to the surface of the device according to common methods of preparing similar osmotic devices which are known to those of ordinary skill such as applying to its surface solids in solution or suspension through the use of a sprayer that spreads them uniformly over the core or by employing nucleated compression or other suitable methods known to those of ordinary skill in the art. The external coat can comprise poly(vinylpyrrolidone) (PVP) and poly(ethylene glycol) (PEG) and can further comprise materials such as, by way of example and without limitation, hydroxypropyl methylcellulose (HPMC), ethylcellulose (EC), hydroxyethylcellulose (HEC), sodium carboxymethyl-cellulose (CMC), dimethylaminoethyl methacrylate-methacrylic acid ester copolymer, ethylacrylate-methylmethacrylate copolymer (GA-MMA), C-5 or 60 SH-50 (Shin-Etsu Chemical Corp.) and combinations thereof. The active agent-containing external coat can also comprise dissolution aids, stability modifiers, and bioabsorption enhancers.

When the external coat comprises a combination of materials, the relative amounts and ratios of those materials can be varied as desired. For example, when the external coat comprises PVP and PEG, the ratio of PVP:PEG can vary as needed, e.g., from about 3-60% by weight of PVP: about 0.1-30% by weight of PEG based upon the weight of the external coat.

The external coat can also comprise a second active agent generally present in an amount ranging from about 0.1 to 99% by weight of the coat. This wide range provides great latitude in the design and application of the osmotic device. Those of ordinary skill in the art will appreciate that the particular amount of second active agent employed will vary according to, among other things, the identity and physical properties and characteristics of the second active agent, the intended application of the osmotic device, the desired effect the second active agent is intended to have, and the physiological condition, if any, being treated.

The preformed passageway in the wall is typically generated by mechanical means, such as perforation by a laser or drill, or any other similar method known to those of ordinary skill in the art. The passageway is generally formed by controlled laser perforation, using an apparatus similar to that disclosed in Theeuwes et al. '864, the entire disclosure of which is incorporated herein by reference. Specific embodiments of the controlled laser perforation method will vary according to the equipment used. The laser equipment of Theeuwes et al. '864 can be modified as described herein to prepare an osmotic device according to the invention. For example, the laser pulse width and pulse period can be varied, as can the total exposure time of an osmotic device to the laser, and as can the linear velocity of an osmotic device traveling under the path of the laser pulse. Other suitable laser equipment, are methods of use thereof, are disclosed in Emerton et al. '793 and Roy '771, the entire disclosures of which are hereby incorporated by reference. The process and system of Faour (U.S. Pregrant Patent Publication No. 2002/0099361) can also be used to form the preformed passageway and/or etch the wall.

Figure 5:
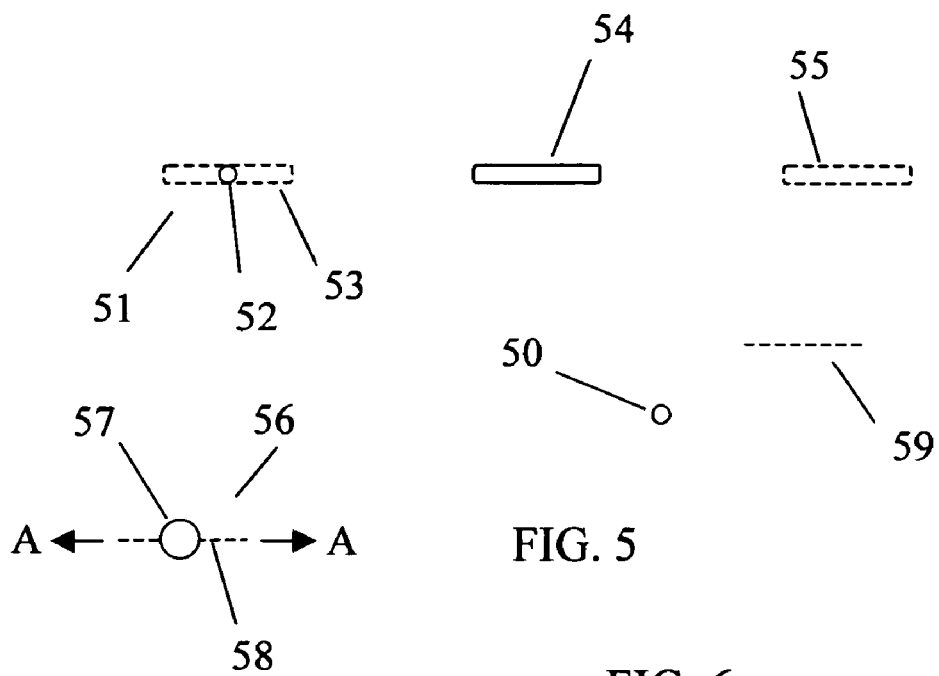
FIG. 5 depicts various alternate embodiments for a preformed aperture according to the invention.

According to one embodiment of the invention, at least one coated core is moved along a predetermined path in a laser apparatus at a predetermined linear velocity that is greater than the velocity used to make similar osmotic devices that do not have passageways that increase in size during use. The coated core is tracked at the predetermined velocity with a laser having a wavelength that is absorbable by the coating. During the tracking, a laser beam, which comprises sequential individual pulses, is then fired at a predetermined section of the coated core for a predetermined period of time and with a predetermined pulse period. The pulse period is the period of time measured from the beginning of a first individual pulse to the beginning of the next individual pulse of the laser beam. The laser beam is also adjusted to fire with a predetermined pulse width, which is the amount of time from the beginning of an individual pulse to the end of that same individual pulse. By controlling the three pulse parameters and the liner velocity, passageways as depicted in FIG. 5 can be prepared.

A preformed passageway can be made to substantially retain its size during use of the device or it can be made to increase in size during use of the dosage form. Preformed passageways of different sizes, shapes and functions, such as those depicted in FIG. 5 can be formed. The passageway (51) includes a central circular hole (52) that penetrates the semipermeable membrane, and two laterally extending portions (53), which are scored, or etched, regions, that do not penetrate the semipermeable membrane. When this passageway is used, the semipermeable membrane tears or dissolves along the etched regions to form the enlarged preformed passageway. The laterally extending regions can be any length desired. The passageway (54) is oval- or slot-shaped, and it penetrates the semipermeable membrane. When it is used, the preformed passageway will generally tend to tear at the ends of the slot. The passageway (55) is scored on the surface of the semipermeable membrane. The scored region (55) ruptures during use to form the actual passageway through which active agent is released. This preformed passageway can continue to tear along the direction of the score or it can tear in random directions. The passageway (56) is similar to the passageway (51) except that these scored regions (58) have a much narrower width and depth than the other scored regions (53). The passageway (59) is actually a scored region on the semipermeable membrane that ruptures during use of the osmotic device. The passageways (50, 51, 54, 55, 56, and 59) are generally formed with a laser. The passageways (51, 54, 55, 56, and 59) will generally increase in size in a predetermined manner during use, i.e., generally in a direction extending along the lateral axes of the passageways. The preformed passageway does not require etchings or scored regions at its edge in order to increase in size during use.

The preformed passageway in the wall may dissolve or tear in a predetermined or random manner, and the shape of the preformed passageway after enlargement can be made to approximate a predetermined or randomly determined shape. The extent to which a passageway increases in size can also be related to the viscosity, molecular weight or degree of substitution of the at least one excipient. Generally, increasing the viscosity, molecular weight, or degree of substitution of the at least one excipient will increase the extent to which the passageway increases in size.

Even if a preformed passageway that increases in size is present in the dosage form, the wall (membrane(s), coating(s), lamina(s)) enveloping the core will still rupture at a location spaced away from the preformed passageway.

Although the controlled release device is depicted with a single preformed passageway, a device according to the present invention can comprise one or more preformed passageways including two, three, four, five, six, seven, eight, nine, ten or more preformed passageways. It is only necessary that the preformed passageways together are adapted to limit the release of ingredients from the core thereby causing an increase in the internal osmotic pressure of the device during use and causing the wall to rupture.

Many common materials known by those of ordinary skill in the art are suitable for use as the semipermeable membrane. Exemplary materials include cellulose esters, cellulose ethers and cellulose esters-ethers. However, it has been found that a semipermeable membrane consisting essentially of cellulose acetate (CA) and poly(ethylene glycol) (PEG), in particular PEG 400, is preferred when used in combination with the other materials required in the present osmotic device. This particular combination of CA and PEG provides a semipermeable membrane that gives the osmotic device a well controlled release profile for the active agent in the core and that retains its chemical and physical integrity in the environment of use. The ratio of CA:PEG generally ranges from about 50-99% by weight of CA: about 50-1% by weight of PEG, and generally about 95% by weight of CA: about 5% by weight of PEG. The ratio can be varied to alter permeability and ultimately the release profile of the osmotic device. Other preferred materials can include a selected member of the group of cellulose acylates such as cellulose acetate, cellulose diacetate, cellulose triacetate and combinations thereof. Many suitable polymers, include those disclosed in Argentine Patent No. 199,301 and other references cited herein, the disclosures of which are hereby incorporated by reference.

The core of the osmotic device of the present invention will comprise an active agent and an osmotic agent and can further comprise many other materials as discussed herein. The amount of active agent present can vary as described above for the external coat. Generally, the active agent will be present in an amount ranging from 0.1-99.9% by weight of the uncoated core. Specific ranges will vary according to the active agent used and the intended use of the osmotic device.

When the active agent is of limited solubility in the environment of use, osmotically effective solutes or osmotic agents, i.e. osmagents, that are capable of being totally or partially solubilized in the fluid, are added. These osmagents will aid in either the suspension or dissolution of the active agent in the core. Exemplary osmagents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art.

These osmagents can also be incorporated to the core of the osmotic device to control the release of an active agent therein. When the agent is only partially or incompletely soluble in the fluid of an environment of use, it can be released as a suspension provided sufficient fluid has been imbibed or absorbed by the core to form a suspension.

One or more osmopolymers can also be added to the core of the device to aid in the delivery of active agents. Osmopolymers are well known to those of ordinary skill in the osmotic device art and well described in the patent and scientific literature. Exemplary osmopolymers include hydrophilic polymers that swell upon contact with water. Osmopolymers may be of plant or animal origin, or synthetic. Examples of osmopolymers include: poly(hydroxy-alkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross-linked with glyoxal, formaldehyde or glutaraldehyde and having a degree of polymerization of 200 to 30,000, a mixture of methyl cellulose, cross-linked agar and carboxymethylcellulose, a mixture of hydroxypropyl methylcellulose and sodium carboxymethylcellulose, polymers of N-vinyl-lactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross-linked indene-maleic anhydride polymers, Good-Rite™ polyacrylic acids having molecular weights of 80,000 to 200,000, Polyox™ polyethylene oxide polymers having molecular weights of 100,000 to 5,000,000, starch graft copolymers, and Aqua-Keeps™ acrylate polymer polysaccharides. These materials swell or expand to an equilibrium state when exposed to water or other biological fluids. This volume expansion is used to physically force the pharmaceutical agent out through openings that have been formed in the wall, shell or coating during manufacture. A water insoluble active agent is primarily released as insoluble particles, which therefore have limited bioavailability. Exemplary osmopolymers are disclosed in U.S. Pat. No. 5,422,123; U.S. Pat. No. 4,783,337; U.S. Pat. No. 4,765,989; U.S. Pat. No. 4,612,008; U.S. Pat. No. 4,327,725; U.S. Pat. No. 4,609,374; U.S. Pat. No. 4,036,228; U.S. Pat. No. 4,992,278; U.S. Pat. Nos. 4,160,020; 4,615,698. The osmopolymers generally swell or expand to a very high degree, usually exhibiting a 2 to 60 fold volume increase. The osmopolymers can be non-cross-linked or cross-linked. The swellable, hydrophilic polymers are, in one embodiment, lightly cross-linked, such as cross-links being formed by covalent or ionic bonds.

As used herein, the term "brittling agent" refers to a compound or composition that renders the semipermeable membrane more susceptible to rupture during use thereby facilitating increasing the size of the preformed passageway.

The osmotic device of the invention can also comprise adsorbents, antioxidants, buffering agents, colorants, flavorants, sweetening agents, tablet antiadherents, tablet binders, tablet and capsule diluents, tablet direct compression excipients, tablet disintegrants, tablet glidants, tablet lubricants, tablet or capsule opaquants, colorant and/or tablet polishing agents.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "tablet antiadherents" is intended to mean agents which prevent the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "tablet binders" is intended to mean substances used to cause adhesion of powder particles in tablet granulations. Such compounds include, by way of example and without limitation, acacia, alginic acid, carboxymethylcellulose sodium, poly(vinylpyrrolidone), compressible sugar (e.g., NuTab™), ethylcellulose, gelatin, liquid glucose, methylcellulose, povidone and pregelatinized starch and other materials known to one of ordinary skill in the art.

When needed, binders may also be included in the present device. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, gelatin, cellulosics in nonaqueous solvents, combinations thereof and others known to those of ordinary skill. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "tablet diluent" or "fillers" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "tablet direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "tablet glidant" is intended to mean agents used in tablet and capsule formulations to promote the flowability of a granulation. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "tablet opaquant" is intended to mean a compound used to render a capsule or a tablet coating opaque. May be used alone or in combination with a colorant. Such compounds include, by way of example and without limitation, titanium dioxide and other materials known to one of ordinary skill in the art.

As used herein, the term "tablet polishing agent" is intended to mean a compound used to impart an attractive sheen to coated tablets. Such compounds include, by way of example and without limitation, carnauba wax, and white wax and other materials known to one of ordinary skill in the art.

As used herein, the term "tablet disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose (e.g., Avicel), carboxymethylcellulose calcium, cellulose polyacrilin potassium (e.g., Amberlite), alginates, sodium starch glycolate, gums such as agar, guar, locust bean, karaya, pectin, tragacanth and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean at compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

The present device can also employ one or more commonly known surface active agents or cosolvents that improve wetting or disintegration of the osmotic device core or layers.

It is contemplated that the osmotic device of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, polysorbate, fatty amine oxides, fatty acid alkanolamides, and poly(oxyethylene)-block-poly(oxypropylene) copolymers, diethylene glycol monostearate, sodium lauryl sulfate, sorbitan monooleate, polyoxyethylene sorbitan fatty acid esters, polysorbate, bile salts, glyceryl monostearate, PLURONIC® line (BASF), and the like; and amphoteric detergents, for example, alkyl aminopropionates and 2-alkylimidazoline quaternary ammonium salts; and mixtures thereof.

Various other components, not otherwise listed above, can be added to the present formulation for optimization of a desired active agent release profile including, by way of example and without limitation, glycerylmonostearate, nylon, cellulose acetate butyrate, d, 1-poly(lactic acid), 1,6-hexanediamine, diethylenetriamine, starches, derivatized starches, acetylated monoglycerides, gelatin coacervates, poly (styrene-maleic acid) copolymer, glycowax, castor wax, stearyl alcohol, glycerol palmitostearate, poly(ethylene), poly(vinyl acetate), poly(vinyl chloride), 1,3-butylene-glycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

Active agents include physiological substances or pharmacological active substances that produce a systemic or localized effect or effects on animals and human beings. Active agents also include pesticides, herbicides, insecticides, antioxidants, plant growth instigators, sterilization agents, catalysts, chemical reagents, food products, nutrients, cosmetics, vitamins, sterility inhibitors, fertility instigators, microorganisms, flavoring agents, sweeteners, cleansing agents and other such compounds for pharmaceutical, veterinary, horticultural, household, food, culinary, agricultural, cosmetic, industrial, cleansing, confectionery and flavoring applications. The active agent can be present in its neutral, ionic, salt, basic, acidic, natural, synthetic, diastereomeric, isomeric, enantiomerically pure, racemic, hydrate, chelate, derivative, analog, or other common form.

Representative active agents include nutrients and nutritional agents, hematological agents, endocrine and metabolic agents, cardiovascular agents, renal and genitourinary agents, respiratory agents, central nervous system agents, gastrointestinal agents, anti-infective agents, biologic and immunological agents, dermatological agents, ophthalmic agents, antineoplastic agents, and diagnostic agents. Exemplary nutrients and nutritional agents include as minerals, trace elements, amino acids, lipotropic agents, enzymes and chelating agents. Exemplary hematological agents include hematopoietic agents, antiplatelet agents, anticoagulants, coumarin and indandione derivatives, coagulants, thrombolytic agents, antisickling agents, hemorrheologic agents, antihemophilic agents, hemostatics, plasma expanders and hemin. Exemplary endocrine and metabolic agents include sex hormones, uterine-active agents, bisphosphonates, antidiabetic agents, glucose elevating agents, adrenocortical steroids, parathyroid hormone, thyroid drugs, growth hormones, posterior pituitary hormones, octreotide acetate, imiglucerase, calcitonin-salmon, sodium phenylbutyrate, betaine anhydrous, cysteamine bitartrate, sodium benzoate and sodium phenylacetate, bromocriptine mesylate, cabergoline, agents for gout, and antidotes.

Exemplary cardiovascular agents include nootropic agents, antiarrhythmic agents, calcium channel blocking agents, vasodilators, antiadrenergics/sympatholytics, renin angiotensin system antagonists, antihypertensive combinations, agents for pheochromocytoma, agents for hypertensive emergencies, antihyperlipidemic agents, antihyperlipidemic combination products, vasopressors used in shock, potassium removing resins, edetate disodium, cardioplegic solutions, agents for patent ductus arteriosus, and sclerosing agents. Exemplary renal and genitourinary agents include interstitial cystitis agents, cellulose sodium phosphate, anti-impotence agents, acetohydroxamic acid (aha), genitourinary irrigants, cystine-depleting agents, urinary alkalinizers, urinary acidifiers, anticholinergics, urinary cholinergics, polymeric phosphate binders, vaginal preparations, and diuretics. Exemplary respiratory agents include bronchodilators, leukotriene receptor antagonists, leukotriene formation inhibitors, nasal decongestants, respiratory enzymes, lung surfactants, antihistamines, nonnarcotic antitussives, and expectorants. Exemplary central nervous system agents include CNS stimulants, narcotic agonist analgesics, narcotic agonist-antagonist analgesics, central analgesics, acetaminophen, salicylates, nonnarcotic analgesics, nonsteroidal anti-inflammatory agents, agents for migraine, antiemetic/antivertigo agents, antianxiety agents, antidepressants, antipsychotic agents, cholinesterase inhibitors, nonbarbiturate sedatives and hypnotics, nonprescription sleep aids, barbiturate sedatives and hypnotics, general anesthetics, anticonvulsants, muscle relaxants, antiparkinson agents, adenosine phosphate, cholinergic muscle stimulants, disulfuram, smoking deterrents, riluzole, hyaluronic acid derivatives, and botulinum toxins. Exemplary gastrointestinal agents including H pylori agents, histamine H2 antagonists, proton pump inhibitors, sucralfate, prostaglandins, antacids, gastrointestinal anticholinergics/antispasmodics, mesalamine, olsalazine sodium, balsalazide disodium, sulfasalazine, celecoxib, infliximab, esomeprazole, famotidine, lansoprazole, omeprazole, pantoprazole, rabeprazole, tegaserod maleate, laxatives, antidiarrheals, antiflatulents, lipase inhibitors, GI stimulants, digestive enzymes, gastric acidifiers, hydrocholeretics, gallstone solubilizing agents, mouth and throat products, systemic deodorizers, and anorectal preparations. Exemplary anti-infective agents including penicillins, such as amoxicilin, cephalosporins and related antibiotics, carbapenem, monobactams, chloramphenicol, quinolones, fluoroquinolones, tetracyclines, macrolides, such as azithromycin, clarithromycin, and the like, spectinomycin, streptogramins, vancomycin, oxalodinones, lincosamides, oral and parenteral aminoglycosides, colistimethate sodium, polymyxin B sulfate, bacitracin, metronidazole, sulfonamides, nitrofurans, methenamines, folate antagonists, antifungal agents, such as fluconazole, voriconazole, and the like, antimalarial preparations, antituberculosis agents, amebicides, antiviral agents, antiretroviral agents, leprostatics, antiprotozoals, anthelmintics, and CDC anti-infective agents. Exemplary biologic and immunological agents including immune globulins, monoclonal antibody agents, antivenins, agents for active immunization, allergenic extracts, immunologic agents, and antirheumatic agents. Exemplary antineoplastic agents include alkylating agents, antimetabolites, antimitotic agents, epipodophyllotoxins, antibiotics, hormones, enzymes, radiopharmaceuticals, platinum coordination complex, anthracenedione, substituted ureas, methylhydrazine derivatives, imidazotetrazine derivatives, cytoprotective agents, DNA topoisomerase inhibitors, biological response modifiers, retinoids, rexinoids, monoclonal antibodies, protein-tyrosine kinase inhibitors, porfimer sodium, mitotane (o, p'-ddd), and arsenic trioxide. Exemplary diagnostic agents include in vivo diagnostic aids, in vivo diagnostic biologicals, and radiopaque agents.

Representative antibacterial substances are beta-lactam antibiotics, tetracyclines, chloramphenicol, neomycin, gramicidin, bacitracin, sulfonamides, aminoglycoside antibiotics, tobramycin, nitrofurazone, nalidixic acid, penicillin, tetracycline, oxytetracycline, chlorotetracycline, erythromycin, cephalosporins and analogs and the antimicrobial combination of fludalanine/pentizidone. Other representative, antibacterial agents include of the poorly water-soluble pyridone-carboxylic acid type such as benofloxacin, nalidixic acid, enoxacin, ofloxacin, amifloxacin, flumequine, tosfloxacin, piromidic acid, pipemidic acid, miloxacin, oxolinic acid, cinoxacin, norfloxacin, ciprofloxacin, pefloxacin, lomefloxacin, enrofloxacin, danofloxacin, binfloxacin, sarafloxacin, ibafloxacin, difloxacin and salts thereof.

Representative antiparasitic compounds are ivermectin, bephenium, hydroxynaphthoate, praziquantel, nifurtimox, benznidasol, dichlorophen and dapsone. Representative antimalarial compounds are 4-aminoquinolines, 8-aminoquinolines and pyrimethamine.

Representative antiviral compounds are protease inhibitors, neuramidinase inhibitors, commercially available compounds, acyclovir and interferon.

Representative anti-inflammatory drugs include rofecoxib, celecoxib, etodolac, flurbiprofen, ibuprofen, ketoprofen, ketorolac, nabumetone, piroxicam, suprofen, tolmetin, zileuton, steroids, cyclooxygenase inhibitors, cortisone, hydrocortisone, betamethasone, dexamethasone, fluocortolone, prednisolone, phenylbutazone, triamcinolone, sulindac, indomethacin, salicylamide, naproxen, colchicine, fenoprofen, diclofenac, indoprofen, dexamethasone, allopurinol, oxyphenbutazone, probenecid and sodium salicylamide.

Representative analgesic drugs are diflunisal, aspirin, ibuprofen, profen-type compounds, morphine, codeine, levorphanol, hydromorphone, oxymorphone, oxycodone, hydrocodone, naloxene, levallorphan, etorphine, fentanyl, hremazocine, meperidine, nalorphine, tramadol, and acetaminophen.

Representative antihistamines and decongestants are acrivastine, astemizole, norastemizol, brompheniramine, cetirizine, clemastine, diphenhydramine, ebastine, famotidine, fexofenadine, meclizine, nizatidine, perilamine, promethazine, ranitidine, terfenadine, chlorpheniramine, cimetidine, tetrahydrozoline, tripolidine, loratadine, desloratadine, antazoline, and pseudoephedrine.

Representative antiasthma drugs are theophylline, ephedrine, beclomethasone dipropionate and epinephrine.

Representative anticoagulants are heparin, bishydroxycoumarin, and warfarin.

Representative psychic energizers are isocoboxazid, nialamide, phenelzine, imipramine, tranycypromine, and parglyene.

Representative anticonvulsants are clonazepam, Phenobarbital, mephobarbital, primidone, enitabas, diphenylhydantion, ethltion, pheneturide, ethosuximide, diazepam, phenyloin carbamazepine, lamotrigine, lorazepam, levetiracetam, oxcarbazepine, topiramate, valproic acid, chlorazepate, gabapentin, felbamate, tiagabine and zonisamide.

Representative antidepressants are amitriptyline, chlordiazepoxide perphenazine, protriptyline, imipramine, doxepin, venlafaxine, o-desmethyl venlafaxine, citalopram, escitalopram, bupropion, clomipramine, desipramine, nefazodone, fluoxetine, fluvoxamine, maprotiline, mirtazapine, nortriptyline, paroxetine, phenelzine, tranylcypromine, sertraline, trazodone, trimipramine, and amoxapine.

Representative antidiabetics are sulphonylureas, such as tolbutamide, chlorpropamide, tolazamide, acetohexamide, glibenclamide, gliclazide, 1-butyl-3-metanilylurea, carbutamide, glibonuride, glipizide, glyburide, gliquidone, glisoxepid, glybuthiazole, glibuzole, glyhexamide, glymidine, glypinamide, phenbutamide, and tolcyclamide; thiazolidinediones (glitazones), such as rosiglitazone, pioglitazone, and troglitazone; biguanidines, such as metformin; and other antidiabetic agents, such as nateglinide, repaglinide, insulin, somatostatin and its analogs, chlorpropamide, isophane insulin, protamine zinc insulin suspension, globin zinc insulin, and extended insulin zinc suspension.

Representative antineoplastics are chlorambucil, cyclophosphamide, triethylenemelamine, thiotepa, hexamethylmelamine, busulfan, carmustine, lomustine, dacarbazine, arabinoside cytosine, mercaptopurine, azathiprine, vincristine, vinblastine, taxol, etoposide, actinomycin D, daunorubicin, doxorubicin, bleomycin, mitomycin; cisplatin; hydroxyurea, procarbazine, aminoglutethimide, tamoxifen, adriamycin, fluorouracil, methotrexate, mechlorethamine, uracil mustard, 5-fluorouracil, 6-6-thioguanine and procarbazine asparaginase.

Representative steroidal drugs are prednisone, prednisolone, cortisone, cortisol and triamcinolone; androgenic steroids such as methyltesterone, and fluoxmesterone; estrogenic steroids such as 17β-estradiol, α-estradiol, estriol, α-estradiol 3 benzoate, and 17-ethynylestradiol-3-methyl ether; progestational steroids such as progesterone, 19-nor-pregn-4-ene-3,20-dione, 17-hydroxy-19-nor-17-α-pregn-5(10)-ene-20-yn-3-one, 17α-ethynyl-17-hydroxy-5(10)-estren-3-one, and 9β, 10α-pregna-4,6-diene-3,20-dione.

Representative estrogen antagonist-agonist drugs are clomiphene citrate and raloxifene HCl.

Representative antipsychotics are prochlorperazine, lithium carbonate, lithium citrate, thioridazine, molindone, fluphenazine, trifluoperazine, perphenazine, amitriptyline, trifluopromazine, chlorpromazine, clozapine, haloperidol, loxapine, mesoridazine, olanzapine, quetiapine, ziprasidone, risperidone, pimozide, mesoridazine besylate, chlorprothixene, and thiothixene.

Representative hypnotics and sedatives are pentobarbital sodium, phenobarbital, secobarbital, thiopental, heterocyclic hypnotics, dioxopiperidines, imidazopyridines, such as zolpidem tartrate, glutarimides, diethylisovaleramide, α-bromoisovaleryl urea, urethanes, disulfanes.

Representative antihypertensives are nifedipine, verapamil, diltiazem, felodipine, amlodipine, isradipine, nicardipine, nisoldipine, nimodipine, bepridil, enalapril, captopril, lisinopril, benazepril, enalaprilat, espirapril, fosinopril, moexipril, quinapril, ramipril, perindopril, trandolapril, furosemide, bumetanide, ethacrynic acid, torsemide, muzolimide, azosemide, piretanide, tripamide, hydrochlorothiazide, chlorthalidone, indapamide, metozalone, cyclopenthiazide, xipamide, mefruside, dorzolamide, acetazolamide, methazolamide, ethoxzolamide, cyclothiazide, clopamide, dichlorphenamide, hydroflumethiazide, trichlormethiazide, polythiazide, benzothiazide, spironolactone, methyldopa, hydralazine, clonidine, chlorothiazide, deserpidine, timolol, propranolol, metoprolol, pindolol, acebutolol, prazosin hydrochloride, methyl dopa (L-β-3,4-dihydroxyphenylalanine), pivaloyloxyethyl ester of α-methyldopa hydrochloride dihydrate, candesartan cilexetil, eprosartan mesylate, losartan potassium, olmersartan medoxomil, telmisartan, valsartan, and reserpine.

Representative tranquilizers are chloropromazine, promazine, fluphenazine, reserpine, deserpidine, meprobamate, and benezodiazepines (anxyiolitic, sedatives, and hypnotics) such as alprazolam, chlordiazepoxide, diazepam, lorazepam, oxazepam, temazepam, and triazolam.

Representative anti-spasmodics and muscle contractants are atropine, scopolamine, methscopolamine, oxyphenonium, papaverine, and prostaglandins such as $PGE_1$ $PGE_2$ $PGF_{1\alpha}$ $PGF_{2\alpha}$, and PGA.

Representative local anesthetics are benzocaine, procaine, lidocaine, maepaine, piperocaine, tetracaine and dibucaine.

Representative muscle relaxants are alcuronium, alosetron, aminophylline, baclofen, carisoprodol, chlorphenesin, chlorphenesin carbamate, chlorzoxazone, chlormezanone, dantrolene, decamethonium, dyphylline, eperisione, ethaverine, gallamine triethiodide, hexafluorenium, metaxalone, metocurine iodide, orphenadrine, pancuronium, papaverine, pipecuronium, theophylline, tizanidine, tolperisone, tubocurarine, vecuronium, idrocilamide, ligustilide, cnidilide, senkyunolide, succinylcholine-chloride, danbrolene, cyclobenzaprine, methocarbamol, diazepam, mephenesin, methocarbomal, trihexylphenidyl, pridinol (pridinolum), and biperiden.

Representative anti-Parkinson agents are carbidopa, levodopa, ropinirole, pergolide mesylate, rasagiline, pramipexole, entacapone, benzacide, bromocriptine, selegiline, mantadine, trihexylphenidyl, biperidene, pridinol mesylate, and tolcapone.

Representative anti-Dementia and anti-Alzheimer disease agents are memantine, donepexil, galantamine, rivastigmine, and tacrine.

Representative sympathomimetic drugs are albuterol, epinephrine, amphetamine ephedrine and norepinephrine.

Representative cardiovascular drugs are procainamide, procainamide hydrochloride, amyl nitrite, nitroglycerin, dipyredamole, sodium nitrate and mannitol nitrate.

Representative diuretics are chlorathiazide, acetazolamide, methazolamide, triamterene, furosemide, indapamide, and flumethiazide.

Representative β-blockers are caravedilol, pindolol, propranolol, practolol, metoprolol, esmolol, oxprenolol, timolol, atenolol, alprenolol, and acebutolol.

Representative phosphodiesterase inhibitors are vardenafil HCl and sildenafil citrate.

Representative antilipemic agents are atorvastatin, cerivastatin, clofibrate, fluvastatin, gemfibrozil, lovastatin, mevinolinic acid, niacin, pravastatin, and simvastatin.

Representative antigout drugs are colchicine, allopurinol, probenecid, sulfinpyrazone, and benzbromadone.

Representative nutritional agents are ascorbic acid, niacin, nicotinamide, folic acid, choline biotin, panthothenic acid, and vitamin $B_{12}$, essential amino acids; essential fats.

Representative ophthalmic agents are pilocarpine, pilocarpine salts such as pilocarpine nitrate, pilocarpine hydrochloride, dichlophenamide, atropine, atropine sulfate, scopolamine and eserine salicylate.

Representative electrolytes are calcium gluconate, calcium lactate, potassium chloride, potassium sulfate, sodium chloride, potassium fluoride, ferrous lactate, ferrous gluconate, ferrous sulfate, ferrous fumurate and sodium lactate.

Representative drugs that act on α-adrenergic receptors are clonidine hydrochloride, prazosin, tamsulosin, terazosin, and doxazosin.

Representative mild CNS stimulants are caffeine, modafinil, and methylphenidate hydrochloride.

The formulation of the invention can also be use with unclassified therapeutic agents such as clopidrogel, which is indicated for the reduction of atherosclerotic events (myocardial infarction, stroke, and vascular death) in patients with atherosclerosis documented by recent stroke, recent myocardial infarction, or established peripheral arterial disease.

The formulation of the invention can also be used to deliver two or more different active agents. Particular combinations of active agents can be provided by the present controlled release device. Some combinations of active agents include: 1) a first drug from a first therapeutic class and a different second drug from the same therapeutic class; 2) a first drug from a first therapeutic class and a different second drug from a different therapeutic class; 3) a first drug having a first type of biological activity and a different second drug having about the same biological activity; 4) a first drug having a first type of biological activity and a different second drug having a different second type of biological activity, 5) the first active agent is pridinol and the second active agent is a selective or specific COX-II inhibitor agent; 6) the first drug is an analgesic agent and the second drug is an anti-inflammatory agent; 7) the analgesic and anti-inflammatory agents are selected from the group consisting of an non-steroidal anti-inflammatory agent, a steroidal anti-inflammatory agent, an opioid receptor agonist agent, and a selective or specific COX-II inhibitor agent; 8) the first and second agents are antihypertensive agents selected from the group consisting of a calcium channel blocker agent, an angiotensin converting enzyme inhibitor agent, a diuretic agent and a beta-adrenergic antagonist agent; 9) the first and second agents are diabetic agents selected from the following main groups of oral antidiabetic drugs available: sulphonylureas, such as tolbutamide, chlorpropamide, tolazamide, acetohexamide, glibenclamide, gliclazide, 1-butyl-3-metanilylurea, carbutamide, glibonuride, glipizide, glyburide, gliquidone, glisoxepid, glybuthiazole, glibuzole, glyhexamide, glymidine, glypinamide, phenbutamide, and tolcyclamide; thiazolidinediones (glitazones), such as rosiglitazone, pioglitazone, and troglitazone; biguanidines, such as metformin; and other antidiabetic agents, such as nateglinide and repaglinide; 10) the first drug is a decongestant and the second drug is an antihistamine; 11) the first drug and the second drug are anti-incontinence drugs; 12) the anti-incontinence drugs are selected from the group consisting of oxybutynin, tolterodine, and darifenacin; 13) the first drug is an antidepressant and the second drug is far the treatment of Dementia; 14) the first drug is an antidepressant and the second drug is an antianxiety drug; 15) the first drug is an antidepressant and the second drug is an antipsychotic drug; 16) the first drug is an antianxiety drug and the second drug is for the treatment of Dementia; 17) the first drug is an antianxiety drug and the second drug is an antipsychotic drug; 18) the first drug is an antianxiety drug and the second drug is an antimanic drug; 19) the first drug is an antipsychotic drug and the second drug is an antimanic drug; 20) the first drug and the second drug are for the treatment of Dementia; 21) the first drug is for the treatment of Dementia and the second drug is an antianxiety drug; 22) the first drug is an anticonvulsant drug and the second drug is an antianxiety drug; 23) the first drug is an anticonvulsant drug and the second drug is an antipsychotic drug; 24) the first drug is an anticonvulsant drug and the second drug is for the treatment of Dementia; 25) the first drug is anticonvulsant and the second drug is an antimanic drug; 26) the first drug is an antiparkinsonian drug and the second drug is an antidepressant; 27) the first drug is an antiparkinsonian drug and the second drug is for the treatment of Dementia; 28) the first drug and the second drug are antiparkinsonian drugs; 29) the first drug and the second drug are mild CNS stimulants; 30) the first drug and the second drug are opioid analgesics; 31) the first drug is an opioid analgesic and the second drug is a non steroidal anti-inflammatory drug; 32) the first drug and the second drug are non steroidal anti-inflammatory drugs; 33) the first drug is a non steroidal anti-inflammatory drug and the second drug is a steroidal drug; 34) the first drug and the second drug are antigout drugs; 31) the first drug and the second drug are antilimepic drugs; and 36) the first drug is carisoprodol and the second drug is diclofenac.

The above-mentioned list should not be considered exhaustive and is merely exemplary of the many embodiments considered within the scope of the invention. Many other active agents can be administered with the formulation of the present invention.

The therapeutic compound(s) contained within the present osmotic device can be formulated as its pharmaceutically acceptable salts. As used herein, "pharmaceutically acceptable salts" refer to derivatives of the disclosed compounds wherein the therapeutic compound is modified by making an acid or base salt thereof. Examples of pharmaceutically acceptable salts include, but are not limited to, mineral or organic acid salts of basic residues such as amines; alkali or organic salts of acidic residues such as carboxylic acids; and others known to those of ordinary skill. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and others known to those of ordinary skill; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill. The pharmaceutically acceptable salts of the present invention can be synthesized from the parent therapeutic compound which contains a basic or acidic moiety by conventional chemical methods. Lists of suitable salts are found in *Remington's Pharmaceutical Sciences,* 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the term vitamin refers to trace organic substances that are required in the diet. For the purposes of the present invention, the term vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term vitamin are the coenzymes thereof. Coenzymes are specific chemical forms of vitamins and can include thiamine pyrophosphates (TPP), flavin mononucleotide (FMN), flavin adenine dinucleotive (FAD), Nicotinamide adenine dinucleotide (NAD), Nicotinamide adenine dinucleotide phosphate (NADP), Coenzyme A (CoA), pyridoxal phosphate, biocytin, tetrahydrofolic acid, coenzyme B12, lipoyllysine, 11-cis-retinal, and 1,25-dihydroxycholecalciferol. The term vitamin(s) also includes choline, carnitine, and alpha, beta, and gamma carotenes.

As used in this disclosure, the term "mineral" refers to inorganic substances, metals, and others known to those of ordinary skill required in the human diet. Thus, the term "mineral" as used herein includes, without limitation, calcium, iron, zinc, selenium, copper, iodine, magnesium, phosphorus, chromium and others known to those of ordinary skill, and mixtures thereof.

The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins, plant extracts, plant powder, herbs, herbal extracts and powders, vitamins, minerals, combinations thereof and others known to those of ordinary skill. As will be appreciated, essentially any dietary supplement may be incorporated into the present osmotic device.

The amount of therapeutic compound incorporated in each device will be at least one or more unit dose and can be selected according to known principles of pharmacy. An effective amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. A dosage form according to the invention that comprises two or more active agents can include subtherapeutic amounts of one or more of those active agents such that an improved, additive or synergistic clinical benefit is provided by the dosage form. By subtherapeutic amount is meant an amount less than that typically recognized as being therapeutic on its own in a subject to which the dosage form is administered. Therefore, a dosage form can comprise a subtherapeutic amount of a first drug and a therapeutic amount of a second drug. Alternatively, a dosage form can comprise a subtherapeutic amount of a first drug and a subtherapeutic amount of a second drug.

As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, generally about 100% or more of the applicable RDA.

For nasal, oral, buccal, and sublingual administration, the device may be in the form of a caplet, tablet or pill. For rectal administration, the device can be included in a suppository, tablet, implant or patch for release of a therapeutic compound into the intestines, sigmoid flexure and/or rectum.

The term "unit dosage form" is used herein to mean a device containing a quantity of the therapeutic compound, said quantity being such that one or more predetermined units may be provided as a single therapeutic administration.

The device of the invention can be prepared according to the methods disclosed herein or those well known in the art. For example, according to one manufacturing technique, the active agent and excipients that comprise the core can be mixed in solid, semisolid or gelatinous form, then moistened and sieved through a specified screen to obtain a granulate.

The granulate is then dried in a dryer and compressed, for example, by punching to form uncoated cores. The compressed and uncoated cores are then covered with a solution of suitable materials that comprise the wall. Subsequently, the wall surrounding each core is perforated with, for example, laser equipment to form the preformed passageway in the manner previously described. Finally, the active agent-containing external coat is optionally applied.

If desired, the device of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein.

The following examples should not be considered exhaustive, but merely illustrative of only a few of the many embodiments contemplated by the present invention. The methods described herein can be followed to prepare osmotic devices according to the invention.

EXAMPLE 1

The following procedure is used to prepare osmotic device tablets containing nifedipine (30, 60, and 90 mg strength) in the core. The osmotic device tablets contain the following ingredients in the amounts indicated:

| Ingredient Nifedipine | Amount (mg) | | |
|---|---|---|---|
| Strength⇒ | 30.0 | 60.0 | 90.0 |
| Core | | | |
| Nifedipine | 33.00 | 66.00 | 99.00 |
| Surfactant | 0.10–2.50 | 0.20–5.00 | 0.30–7.50 |
| Diluent | 20.00–90.00 | 40.00–180.00 | 60.00–270.00 |
| Osmagent | 45.00–214.00 | 90.00–425.00 | 135.00–640.00 |
| Binder | 10.00–50.00 | 20.00–100.00 | 30.00–150.00 |
| Osmopolymer 1 | 35.00–115.00 | 70.00–230.00 | 105.00–345.00 |
| Osmopolymer 2 | 3.00–10.50 | 6.00–21.00 | 9.00–31.50 |
| Glidant | 0.10–6.00 | 0.20–12.00 | 0.30–18.00 |
| Lubricant | 0.10–6.00 | 0.20–12.00 | 0.30–18.00 |
| Purified water* | 20.00–50.00 | 40.00–100.00 | 60.00–150.00 |
| Coating A | | | |
| Cellulose Ester 1 | 18.00–43.00 | 20.00–45.00 | 25.00–50.00 |
| Cellulose Ester 2 | 17.50–32.50 | 19.50–35.00 | 24.50–43.00 |
| Plasticizer | 0.50–5.00 | 0.50–5.00 | 0.50–7.00 |
| Organic solvent* | 450.00–1500.00 | 500.00–1650.00 | 625.00–2050.00 |
| Purified Water* | 80.00–330.00 | 89.00–370.00 | 110.00–460.00 |
| Coating B | | | |
| Opadry Y 30 18084-A | 4.90–29.50 | 7.90–48.80 | 9.80–68.60 |
| Colorant | 0.10–1.00 | 0.10–1.20 | 0.20–1.40 |
| Purified Water* | 80.00–320.00 | 128.00–530.00 | 160.00–750.00 |

*denotes a component used during manufacture of the osmotic device but which is substantially absent in the final dosage form.

First, the core composition is prepared by placing nifedipine, two osmopolymers, a diluent, an osmagent, and a binder in a high shear mixer and mix for 5 minutes. The granulation process is initiated by the gradual addition of a granulating solution containing a surfactant and purified water to the high shear with continuous blending to produce a wet blend. Next, the wet blend is granulated and dried at 40-50° C. for 20 minutes in a fluid bed to remove the water. Then, the dry granules are screened through a 30 USP mesh screen for size reduction. Next, the screened granules are mixed with a glidant and a lubricant, that have been previously passed through a 60 mesh screen, in a V-Blender during 5 minutes. This final blend is tabletted to provide the cores.

A first composition to cover the cores is prepared as follows: two cellulose esters and a plasticizer are added to organic solvent and purified water, and mixed thoroughly to form a polymer solution. This solution is sprayed onto the tablets in a perforated pan coater to form film-coated cores. A 0.5 mm hole is drilled through the coating to provide perforated film-coated tablets.

A finish coat comprising Opadry and a colorant in purified water is applied onto the film-coated tablets to obtain the osmotic device tablets.

EXAMPLE 2

The following procedure is used to prepare osmotic device tablets containing alprazolam (1 and 2 mg strength) in the core. The osmotic device tablets contain the following ingredients in the amounts indicated:

| Ingredient | Amount (mg) | |
|---|---|---|
| Alprazolam Strength⇒ | 1 | 2 |
| Core | | |
| Alprazolam | 1.00 | 2.00 |
| Surfactant | 0.20–1.20 | 0.24–2.16 |
| Diluent | 7.50–67.50 | 15.00–135.00 |
| Osmagent | 8.70–78.30 | 17.40–156.60 |
| Binder | 2.70–24.30 | 5.40–48.60 |
| Osmopolymer 1 | 7.80–70.20 | 15.60–140.40 |
| Osmopolymer 2 | 0.58–5.22 | 1.15–10.50 |
| Glidant | 0.35–3.15 | 0.7–6.30 |
| Lubricant | 0.25–2.25 | 0.50–4.50 |
| Purified water* | 3.80–34.65 | 7.70–69.30 |
| Coating A | | |
| Methacrylate copolymer | 0.60–6.00 | 1.00–10.50 |
| Cellulose Ester 1 | 2.40–22.00 | 3.90–41.50 |
| Cellulose Ester 2 | 2.40–22.00 | 3.90–41.50 |
| Plasticizer | 0.25–2.55 | 0.40–4.00 |
| Organic solvent* | 95.00–855.00 | 150.00–1,375.00 |
| Purified Water* | 16.80–152.00 | 26.00–242.00 |
| Coating B | | |
| Opadry Y 30 18084-A | 2.35–21.50 | 3.90–35.50 |
| Colorant | 0.04–0.35 | 0.06–0.60 |
| Purified Water* | 31.50–286.50 | 40.00–360.00 |

First, the core composition is prepared by placing alprazolam, two osmopolymers, a diluent, an osmagent, and a binder in a high shear mixer and mix for 5 minutes. The granulation process is initiated by the gradual addition of a granulating solution containing a surfactant and purified water to the high shear with continuous blending to produce a wet blend. Next, the wet blend is granulated and dried at 40-50° C. for 20 minutes in a fluid bed to remove the water. Then, the dry granules are screened through a 30 USP mesh screen for size reduction. Next, the screened granules are mixed with a glidant and a lubricant, that have been previously passed through a 60 mesh screen, in a V-Blender during 5 minutes. This final blend is tabletted to provide the cores.

A first composition to cover the cores is prepared as follows: two cellulose esters, a methacrylate copolymer, and a plasticizer are added to organic solvent and purified water, and mixed thoroughly to form a polymer solution. This solution is sprayed onto the tablets in a perforated pan coater to form film-coated cores. A 0.5 mm hole is drilled through the coating to provide perforated film-coated tablets.

A finish coat comprising Opadry and a colorant in purified water is applied onto the film-coated tablets to obtain the osmotic device tablets.

EXAMPLE 3

The following procedure is used to prepare osmotic device tablets containing doxazosin mesylate (1, 2, 4, and 8 mg strength) in the core. The osmotic device tablets contain the following ingredients in the amounts indicated:

tablets in a perforated pan coater to form film-coated cores. A 0.5 mm hole is drilled through the coating to provide perforated film-coated tablets.

A second composition to cover the perforated film-coated tablets is prepared as follows: a water soluble polymer, an opaquant, a glidant, and a colorant are added to an organic solvent and mixed thoroughly to form a polymer solution. This solution is sprayed onto the perforated film-coated tablets in a perforated pan coater to form perforated film-coated tablets coated with a polymer coat.

A finish coat comprising Opadry and a colorant in purified water is applied onto the tablets to obtain the osmotic device tablets.

| Ingredient Doxazosin mesylate | Amount (mg) | | | |
|---|---|---|---|---|
| Strength⇒ | 1.0 | 2.0 | 4.0 | 8.0 |
| Core | | | | |
| Doxazosin mesylate | 1.21 | 2.43 | 4.85 | 9.70 |
| Surfactant | 0.05–1.25 | 0.10–2.50 | 0.20–5.00 | 0.40–10.00 |
| Diluent | 20.00–60.00 | 40.00–120.00 | 80.00–240.00 | 160.00–480.00 |
| Osmagent | 22.50–80.00 | 45.00–160.00 | 90.00–320.00 | 180.00–640.00 |
| Binder | 3.00–25.00 | 6.00–50.00 | 12.00–100.00 | 24.00–200.00 |
| Osmopolymer 1 | 17.00–60.00 | 34.00–120.00 | 64.00–240.00 | 128.00–480.00 |
| Osmopolymer 2 | 1.50–5.50 | 3.00–11.00 | 6.00–22.00 | 12.00–44.00 |
| Glidant | 0.05–3.00 | 0.10–6.00 | 0.20–12.00 | 0.40–24.00 |
| Lubricant | 0.05–3.00 | 0.10–6.00 | 0.20–12.00 | 0.40–24.00 |
| Purified water* | 10.00–25.00 | 20.00–50.00 | 40.00–100.00 | 80.00–200.00 |
| Coating A | | | | |
| Cellulose Ester 1 | 12.60–30.00 | 14.00–32.00 | 15.00–34.00 | 17.00–35.00 |
| Cellulose Ester 2 | 12.25–22.75 | 13.50–24.50 | 14.00–28.00 | 17.00–31.00 |
| Plasticizer | 0.35–3.50 | 0.35–4.00 | 0.35–4.20 | 0.35–5.00 |
| Organic Solvent* | 315.00–1050.00 | 550.00–1150.00 | 370.00–1260.00 | 435.00–1450.00 |
| Purified Water* | 56.00–231.00 | 62.00–260.00 | 67.00–280.00 | 75.00–325.00 |
| Coating C | | | | |
| Water soluble polymer | 1.00–15.00 | 1.60–24.00 | 2.50–38.40 | 4.00–61.50 |
| Opaquant | 1.00–20.00 | 1.60–32.00 | 2.50–52.00 | 4.00–83.20 |
| Antiadherent | 1.00–25.00 | 1.60–40.00 | 2.50–64.00 | 4.00–102.50 |
| Colorant | 0.10–1.00 | 0.16–1.60 | 0.25–2.50 | 0.40–4.00 |
| Organic Solvent* | 30.00–200.00 | 48.00–320.00 | 75.00–512.00 | 120.00–820.00 |
| Coating D | | | | |
| Opadry Y 30 18084-A | 3.40–21.00 | 7.90–48.80 | 8.50–59.00 | 9.80–68.60 |
| Colorant | 0.07–0.70 | 0.10–1.20 | 0.15–1.32 | 0.20–1.40 |
| Purified Water* | 56.00–225.00 | 89.00–370.00 | 95.00–470.00 | 110.00–525.00 |

First, the core composition is prepared by placing doxazosin mesylate, two osmopolymers, a diluent, an osmagent, and a binder in a high shear mixer and mix for 5 minutes. The granulation process is initiated by the gradual addition of a granulating solution containing a surfactant and purified water to the high shear with continuous blending to produce a wet blend. Next, the wet blend is granulated and dried at 40-50° C. for 20 minutes in a fluid bed to remove the water. Then, the dry granules are screened through a 30 USP mesh screen for size reduction. Next, the screened granules are mixed with a glidant and a lubricant, that have been previously passed through a 60 mesh screen, in a V-Blender during 5 minutes. This final blend is tabletted to provide the cores.

A first composition to cover the cores is prepared as follows: two cellulose esters and a plasticizer are added to organic solvent and purified water, and mixed thoroughly to form a polymer solution. This solution is sprayed onto the

EXAMPLE 4

The following procedure is used to prepare osmotic device tablets containing felodipine (2.5, 5.0, and 10 mg strength) in the core. The osmotic device tablets contain the following ingredients in the amounts indicated:

| Ingredient Felodipine | Amount (mg) | | |
|---|---|---|---|
| Strength⇒ | 2.5 | 5.0 | 10.0 |
| Core | | | |
| Felodipine | 2.75 | 5.50 | 10.10 |
| Surfactant | 0.10–2.50 | 0.20–5.00 | 0.30–7.50 |
| Diluent | 40.00–120.00 | 90.00–240.00 | 140.00–360.00 |

-continued

| Ingredient Felodipine | Amount (mg) | | |
|---|---|---|---|
| Strength⇒ | 2.5 | 5.0 | 10.0 |
| Osmagent | 45.00–160.00 | 90.00–160.00 | 135.00–240.00 |
| Binder | 10.00–50.00 | 20.00–100.00 | 30.00–150.00 |
| Osmopolymer 1 | 35.00–115.00 | 70.00–230.00 | 105.00–345.00 |
| Osmopolymer 2 | 3.00–10.50 | 6.00–21.00 | 9.00–31.50 |
| Glidant | 0.10–6.00 | 0.20–12.00 | 0.30–18.00 |
| Lubricant | 0.10–6.00 | 0.20–12.00 | 0.30–18.00 |
| Purified water* | 20.00–50.00 | 40.00–100.00 | 60.00–150.00 |
| Coating A | | | |
| Cellulose Ester 1 | 18.00–43.00 | 20.00–45.00 | 25.00–50.00 |
| Cellulose Ester 2 | 17.50–32.50 | 19.50–35.00 | 24.50–43.00 |
| Plasticizer | 0.50–5.00 | 0.50–5.00 | 0.50–7.00 |
| Organic solvent* | 450.00–1500.00 | 500.00–1650.00 | 625.00–2050.00 |
| Purified Water* | 80.00–330.00 | 89.00–370.00 | 110.00–460.00 |
| Coating B | | | |
| Opadry Y 30 18084-A | 4.90–29.50 | 7.90–48.80 | 9.80–68.60 |
| Colorant | 0.10–1.00 | 0.10–1.20 | 0.20–1.40 |
| Purified Water* | 80.00–320.00 | 128.00–530.00 | 160.00–750.00 |

First, the core composition is prepared by placing felodipine, two osmopolymers, a diluent, an osmagent, and a binder in a high shear mixer and mix for 5 minutes. The granulation process is initiated by the gradual addition of a granulating solution containing a surfactant and purified water to the high shear with continuous blending to produce a wet blend. Next, the wet blend is granulated and dried at 40-50° C. for 20 minutes in a fluid bed to remove the water. Then, the dry granules are screened through a 30 USP mesh screen for size reduction. Next, the screened granules are mixed with a glidant and a lubricant, that have been previously passed through a 60 mesh screen, in a V-Blender during 5 minutes. This final blend is tabletted to provide the cores. A first composition to cover the cores is prepared as follows: two cellulose esters and a plasticizer are added to organic solvent and purified water, and mixed thoroughly to form a polymer solution. This solution is sprayed onto the tablets in a perforated pan coater to form film-coated cores. A 0.5 mm hole is drilled through the coating to provide perforated film-coated tablets.

A finish coat comprising Opadry and a colorant in purified water is applied onto film-coated tablets to obtain the osmotic device tablets.

EXAMPLE 5

A bioequivalence study was conducted comparing the 60 mg nifedipine osmotic device tablets as prepare according to Example 1 with the Procardia XL 60 mg tablets (control formulation). This study was a two-period, single-dose, crossover randomized study with a one-week washout period. Twenty-four healthy hospitalized subjects (non-smokers between the ages of 21-50) were randomly separated into two equally sized groups. The first group received the 60 mg nifedipine osmotic device tablets of Example 1 and the second group received the control formulation in fasting condition during the first period. After the washout period, the first group received the control formulation and the second group received the 60 mg nifedipine osmotic device tablets of Example 1 during a second period. Blood samples were taken periodically from 0 to 72 hrs after administration and plasma aliquots were obtained immediately and stored at −20° C. for later analysis by HPLC to determine nifedipine content. The following pharmacokinetic parameters were calculated from the plasma concentration curve for each formulation and each subject: area under the curve from 0-72 hrs ($AUC_{0-t}$) and extrapolated to infinity ($AUC_{0-inf}$); maximum concentration of nifedipine in plasma ($C_{max}$); and time to reach $C_{max}$ ($T_{max}$). Safety was evaluated by physical examination, vital signs and adverse event records. Statistical comparisons of the main parameter $C_{max}$, $AUC_{0-t}$ and $AUC_{0-inf}$ after logarithmic transformation were carried out by using Analysis of Variance (ANOVA) for the crossover design. The model included terms for the main fixed effects Treatment, Period, Sequence and the random effect Subject nested in Sequence. Geometric mean of Cmax, $AUC_{0-t}$ and $AUC_{0-inf}$ and 90% confidence intervals for the respective test-to-control ratio were calculated in order to evaluate bioequivalence. Bioequivalence was declared if 90% confidence interval limits were within the region 80.00%-125.00% for the three main parameter Cmax, $AUC_{0-t}$ and $AUC_{0-inf}$.

EXAMPLE 6

The following procedure is used to prepare osmotic device tablets containing carisoprodol (400 mg strength) in the core, and carisoprodol (200 mg strength) and rofecoxib (12.5, 25 and 50 mg strength) in the external coat. The osmotic device tablets contain the following ingredients in the amounts indicated:

| Ingredient | Amount (mg) | | |
|---|---|---|---|
| Carisoprodol Strength⇒ | 400.0 | 400.0 | 400.0 |
| Carisoprodol Strength⇒ | 200.0 | 200.0 | 200.0 |
| Rofecoxib Strength⇒ | 12.5 | 25.0 | 50.0 |
| Core | | | |
| Carisoprodol | 400.00 | 400.00 | 400.00 |
| Surfactant | 0.10–0.40 | 0.10–0.40 | 0.10–0.40 |
| Diluent | 10.00–145.00 | 10.00–145.00 | 10.00–145.00 |
| Osmagent | 30.00–60.00 | 30.00–60.00 | 30.00–60.00 |
| Binder | 3.00–20.00 | 3.00–20.00 | 3.00–20.00 |
| Osmopolymer 1 | 20.00–80.00 | 20.00–80.00 | 20.00–80.00 |
| Osmopolymer 2 | 3.00–25.00 | 3.00–25.00 | 3.00–25.00 |
| Glidant | 0.10–2.50 | 0.10–2.50 | 0.10–2.50 |
| Lubricant | 1.00–7.00 | 1.00–7.00 | 1.00–7.00 |
| Purified water* | 15.00–60.00 | 15.00–60.00 | 15.00–60.00 |
| Coating A | | | |
| Cellulose Ester 1 | 5.00–30.00 | 5.00–30.00 | 5.00–30.00 |
| Cellulose Ester 2 | 5.00–30.00 | 5.00–30.00 | 5.00–30.00 |
| Plasticizer | 0.50–3.00 | 0.50–3.00 | 0.50–3.00 |
| Organic solvent* | 100.00–480.00 | 100.00–480.00 | 100.00–480.00 |
| Purified Water* | 25.00–150.00 | 25.00–150.00 | 25.00–150.00 |
| Coating B | | | |
| Carisoprodol | 200.00 | 200.00 | 200.00 |
| Rofecoxib | 12.50 | 25.00 | 50.00 |
| Diluent | 25.00–150.00 | 25.00–150.00 | 25.00–150.00 |
| Binder | 1.50–8.50 | 1.50–8.50 | 1.50–8.50 |
| Plasticizer | 0.50–5.00 | 0.50–5.00 | 0.50–5.00 |
| Glidant | 0.50–6.00 | 0.50–6.00 | 0.50–6.00 |
| Disintegrant | 1.00–30.00 | 1.00–30.00 | 1.00–30.00 |
| Lubricant | 1.00–8.00 | 1.00–8.00 | 1.00–8.00 |
| Purified Water* | 5.00–25.00 | 5.00–25.00 | 5.00–25.00 |
| Coating C | | | |
| Opadry Y 30 18084-A | 5.00–25.00 | 5.00–25.00 | 5.00–25.00 |
| Colorant | 0.05–1.50 | 0.05–1.50 | 0.05–1.50 |
| Purified Water* | 30.00–290.00 | 30.00–290.00 | 30.00–290.00 |

First, the core composition is prepared by placing carisoprodol, a diluent, an osmagent, a binder, and two osmopolymers in a high shear mixer, and mix for 5 minutes. The granulation process is initiated by the gradual addition of a granulating solution containing a surfactant and purified water to the high shear with continuous blending to produce a wet blend. Next, the wet blend is granulated and dried at 40-50° C. for 20 minutes in a fluid bed to remove the water. Then, the dry granules are screened through a 20 USP mesh screen for size reduction. Next, the screened granules are mixed with a glidant and a lubricant, that have been previously passed through a 60 mesh screen, in a V-Blender during 5 minutes. This final blend is tabletted to provide the cores.

A first composition to cover the cores is prepared as follows: two cellulose esters and a plasticizer are added to organic solvent and purified water, and mixed thoroughly to form a polymer solution. This solution is sprayed onto the tablets in a perforated pan coater to form film-coated cores. A 0.5 mm hole is drilled through the coating to provide perforated cores. The perforated cores have an outer diameter of about 12.0 mm.

The perforated cores are subjected to a coating process through compression with a granulate as follows: carisoprodol, rofecoxib, a diluent and a binder are placed in a high shear mixer and mix for 5 minutes. The granulation process is initiated by the gradual addition of a granulating solution containing a plasticizer and purified water to the high shear with continuous blending to produce a wet blend. Next, the wet blend is granulated and dried at 40-50° C. for 20 minutes in a fluid bed to remove the water. Then, the dry granules are screened through a 20 USP mesh screen for size reduction. Next, the screened granules are mixed with a glidant and a lubricant, that have been previously passed through a 60 mesh screen, in a V-Blender during 5 minutes. This resulting granulate is applied over the coated core through compression. The coated device has an outer diameter of about 14 mm.

A finish coat comprising Opadry and a colorant in purified water is applied onto the coated device to obtain the final osmotic device tablets.

EXAMPLE 7

The following procedure is used to prepare osmotic device tablets containing carisoprodol (400 mg strength) in the core, and carisoprodol (200 mg strength) and diclofenac sodium (25, 50 and 75 mg strength) in the external coat. The osmotic device tablets contain the following ingredients in the amounts indicated:

| INGREDIENT | AMOUNT (MG) | | |
|---|---|---|---|
| Inner Carisoprodol Strength→ | 400.0 | 400.0 | 400.0 |
| Outer Carisoprodol Strength→ | 200.0 | 200.0 | 200.0 |
| DICLOFENAC SODIUM STRENGTH→ | 25.0 | 50.0 | 75.0 |
| CORE | | | |
| Carisoprodol | 400.00 | 400.00 | 400.00 |
| Surfactant | 0.10 = 0.40 | 0.10 = 0.40 | 0.10 = 0.40 |
| Diluent | 10.00 = 145.00 | 10.00 = 145.00 | 10.00 = 145.00 |
| Osmagent | 30.00 = 60.00 | 30.00 = 60.00 | 30.00 = 60.00 |
| Binder | 3.00 = 20.00 | 3.00 = 20.00 | 3.00 = 20.00 |
| Osmopolymer 1 | 20.00 = 80.00 | 20.00 = 80.00 | 20.00 = 80.00 |
| Osmopolymer 2 | 3.00 = 25.00 | 3.00 = 25.00 | 3.00 = 25.00 |
| Glidant | 0.10 = 2.50 | 0.10 = 2.50 | 0.10 = 2.50 |
| Lubricant | 1.00 = 7.00 | 1.00 = 7.00 | 1.00 = 7.00 |
| Purified water* | 15.00 = 60.00 | 15.00 = 60.00 | 15.00 = 60.00 |
| Coating A | | | |
| Cellulose Ester 1 | 5.00 = 30.00 | 5.00 = 30.00 | 5.00 = 30.00 |
| Cellulose Ester 2 | 5.00 = 30.00 | 5.00 = 30.00 | 5.00 = 30.00 |
| Plasticizer | 0.50 = 3.00 | 0.50 = 3.00 | 0.50 = 3.00 |
| Organic Solvent* | 100.00 = 480.00 | 100.00 = 480.00 | 100.00 = 480.00 |
| Purified Water* | 25.00 = 150.00 | 25.00 = 150.00 | 25.00 = 150.00 |
| Coating B | | | |
| Carisoprodol | 200.00 | 200.00 | 200.00 |
| Diclofenac sodium | 25.0 | 50.0 | 75.0 |
| Diluent | 12.50 = 140.0 | 12.50 = 130.0 | 12.50 = 130.0 |
| Binder | 1.50 = 8.50 | 1.50 = 8.50 | 1.50 = 8.50 |
| Plasticizer | 0.50 = 5.00 | 0.50 = 5.00 | 0.50 = 5.00 |
| Glidant | 0.50 = 6.00 | 0.50 = 6.00 | 0.50 = 6.00 |
| Disintegrant | 1.00 = 30.00 | 1.00 = 30.00 | 1.00 = 30.00 |
| lubricant | 1.00 = 8.00 | 1.00 = 8.00 | 1.00 = 8.00 |
| Purified Water* | 5.00 = 25.00 | 5.00 = 25.00 | 5.00 = 25.00 |
| Coating C | | | |
| Eudragit S 100 (Methacrylic Acid Copolymer, Type B) | 7.50 = 30.00 | 7.50 = 30.00 | 7.50 = 30.00 |
| Triethyl citrate | 0.80 = 32.00 | 0.80 = 32.00 | 0.80 = 32.00 |
| Talc | 4.20 = 16.80 | 4.20 = 16.80 | 4.20 = 16.80 |
| Isopropyl alcohol | 125.00 = 500.00 | 125.00 = 500.00 | 125.00 = 500.00 |
| Purified water | 7.50 = 30.00 | 7.50 = 30.00 | 7.50 = 30.00 |
| Coating D | | | |
| Opadry Y 30 18084-A | 5.00 = 25.00 | 5.00 = 25.00 | 5.00 = 25.00 |
| Colorant | 0.05 = 1.50 | 0.05 = 1.50 | 0.05 = 1.50 |
| Purified Water* | 30.00 = 290.00 | 30.00 = 290.00 | 30.00 = 290.00 |

First, the core composition is prepared by placing carisoprodol, a diluent, an osmagent, a binder, and two osmopolymers in a high shear mixer, and mix for 5 minutes, The granulation process is initiated by the gradual addition of a granulating solution containing a surfactant and purified water to the high shear with continuous blending to produce a wet blend. Next, the wet blend is granulated and dried at 40-50° C. for 20 minutes in a fluid bed to remove the water. Then, the thy granules are screened through a 20 USP mesh screen for size reduction. Next, the screened granules are mixed with a glidant and a lubricant, that have been previously passed through a 60 mesh screen, in a V-Blender during 5 minutes. This final blend is tabletted to provide the cores.

A first composition to cover the cares is prepared as follows: two cellulose esters and a plasticizer are added to organic solvent and purified water, and mixed thoroughly to form a polymer solution. This solution is sprayed onto the tablets in a perforated pan coater to form film-coated cores. A 0.5 mm hole is drilled through the coating to provide perforated cores. The perforated cores have an outer diameter of about 12.0 mm.

A second composition to cover the perforated coated cores is prepared as follows: carisoprodol, diclofenac sodium, a diluent and a hinder are placed in a high shear mixer and mix for 5 minutes. The granulation process is initiated by the gradual addition of a granulating solution containing a plasticizer and purified water to the high shear with continuous blending to produce a wet blend. Next, the wet blend is granulated and dried at 40-500 for 20 minutes in a fluid bed to remove the water. Then, the dry granules are screened through a 20 USP mesh screen for size reduction. Next, the screened granules are mixed with a glidant and a lubricant, that have been previously passed through a 60 mesh screen, in a V-Blender during 5 minutes. The granulate is applied over the perforated cores through compression to obtain carisoprodol-diclofenac coated osmotic devices. The coated device has an outer diameter of about 14 mm.

A third composition to cover the carisoprodol-diclofenac coated osmotic devices with an enteric coat is prepared as follows: Eudragit S 100, talc, and triethyl citrate are added to the purified water and isopropyl alcohol to form the coating suspension. This suspension is sprayed onto the tablets in a perforated pan coater to obtain enteric-coated osmotic devices.

A finish coat comprising Opadry and a colorant in purified water is applied onto the coated device to obtain the final osmotic device tablets.

EXAMPLE 8

The following procedure is used to prepare osmotic device tablets containing carisoprodol (500 mg strength) in the care, and diclofenac sodium (25, 50 and 25 mg strength) in the coating). The osmotic device tablets contain the following ingredients in the amounts indicated:

| INGREDIENT | AMOUNT (MG) | | |
|---|---|---|---|
| Carisoprodol Strength→ | 500.0 | 500.0 | 500.0 |
| DICLOFENAC SODIUM STRENGTH→ | 25.0 | 50.0 | 75.0 |
| CORE | | | |
| Carisoprodol | 500.00 | 500.00 | 500.00 |
| Polysorbate 20 | 0.15 | 0.15 | 0.15 |
| Mannitol | 62.05 | 62.05 | 62.05 |
| Sodium chloride | 45.00 | 45.00 | 45.00 |
| Povidone | 10.00 | 10.00 | 10.00 |
| Polyethylene oxide | 50.00 | 50.00 | 50.00 |
| Hypromellose | 7.50 | 7.50 | 7.50 |
| Silicon dioxide colloidal | 0.30 | 0.30 | 0.30 |
| Magnesium stearate | 5.00 | 5.00 | 5.00 |
| Purified water* | 30.00 | 30.00 | 30.00 |
| Coating A | | | |
| Cellulose Acetate | 35.00 | 35.00 | 35.00 |
| Polyethylene Glycol 400 | 1.75 | 1.75 | 1.75 |
| Acetone* | 336.20 | 336.20 | 336.20 |
| Purified Water* | 73.80 | 73.80 | 73.80 |
| Coating B | | | |
| Diclofenac sodium | 25.00 | 50.00 | 75.00 |
| Mannitol | 206.00 | 181.00 | 156.00 |
| Povidone | 5.00 | 5.00 | 5.00 |
| Polyethylene Glycol 400 | 2.50 | 2.50 | 2.50 |
| Silicon dioxide colloidal | 3.00 | 3.00 | 3.00 |
| Sodium starch glycolate | 4.50 | 4.50 | 4.50 |
| Magnesium stearate | 4.00 | 4.00 | 4.00 |
| Purified Water* | 12.00 | 12.00 | 12.00 |
| Coating C | | | |
| Eudragit S 100 (Methacrylic Acid Copolymer, Type B) | 24.00 | 24.00 | 24.00 |
| Triethyl citrate | 2.60 | 2.60 | 2.60 |
| Talc | 13.40 | 13.40 | 13.40 |
| Isopropyl alcohol | 400.00 | 400.00 | 400.00 |
| Purified water | 24.00 | 24.00 | 24.00 |
| Coating D | | | |
| Opadry Y 30 18084-A | 25.00 | 25.00 | 25.00 |
| Colorant | 0.30 | 0.30 | 0.30 |
| Purified Water* | 280.00 | 280.0 | 280.00 |

*denotes a component used during manufacture of the osmotic device but which is substantially absent in the final dosage form.

* denotes a component used during manufacture of the osmotic device but which is substantially absent in the final dosage form.

First the core composition is prepared by placing carisoprodol, mannitol, sodium chloride, povidone, polyethylene oxide and hypromellose in a high shear mixer and mix for 5 minutes. The granulation process is initiated by the gradual addition of a granulating solution containing polysorbate 2 μl and purified water to the high shear with continuous blending to produce a wet blend. Next, the wet blend is granulated and dried at 40-50° C. for 20 minutes in a fluid lied to remove the water. Then, the dry granules are screened through a 20 USP mesh screen for size reduction. Next, the screened granules are mixed with silicon dioxide colloidal and magnesium stearate, that have been previously passed through a IQ mesh screen, in a V-Blender during 5 minutes. This final blend is tabletted to provide the cores.

A first composition to cover the cores is prepared as follows cellulose acetate and polyethylene glycol 400 are added to organic solvent and purified water, and mixed thoroughly to form a polymer solution. This solution is sprayed onto the tablets in a perforated pan coater to form film-coated cores. A 0.5 mm hole is drilled through the coating to provide perforated film-coated tablets.

A second composition to cover the perforated coated cores is prepared as follows: diclofenac sodium, mannitol and povidone are mixed for 5 minutes in a high shear mixer. The granulation process is initiated by the gradual addition of a granulating solution containing polyethylene glycol 400 and purified water to the high shear with continuous blending to produce a wet blend. Next, the wet blend is granulated and dried at 40-50° C. for 20 minutes in a fluid bed is remove the water. Then, the dry granules are screened through a 20 USP mesh screen for size reduction. Next, the screened granules are mixed with silicon dioxide colloidal and magnesium stearate, that have been previously passed through a 60 mesh screen, in a V-Blender during 5 minutes. The granulate is applied over the coated core through compression to obtain diclofenac coated osmotic devices. These particular devices have a 14 mm outer diameter and contain a 12.5 mm outer diameter osmotic core, approximately.

A third composition to cover the diclofenac coated osmotic devices with an enteric coat is prepared as follows. Eudragit S 100, talc, and triethyl citrate are added to purified water and isopropyl alcohol to form the coating suspension. This suspension is sprayed onto the tablets in a perforated pan coater to obtain the enteric-coated osmotic device tablets.

A finish coat comprising Opadry and a colorant in purified water is applied onto the enteric-coated osmotic device tablets to obtain the final osmotic device tablets.

EXAMPLE 9

The following procedure is used to prepare osmotic device tablets containing carisoprodol (500 mg strength), and diclofenac sodium (100 and 200 mg strength) in the core. The osmotic device tablets contain the following ingredients in the amounts indicated:

| Ingredient | Amount (mg) | |
|---|---|---|
| Carisoprodol Strength→ | 500.0 | 500.0 |
| DICLOFENAC SODIUM STRENGTH→ | 100.0 | 200.0 |
| CORE | | |
| Carisoprodol | 500.00 | 500.00 |
| Diclofenac Sodium | 100.00 | 200.00 |
| Polysorbate 20 | 0.16 | 0.18 |

-continued

| Ingredient | Amount (mg) | |
|---|---|---|
| Mannitol | 80.26 | 108.46 |
| Sodium chloride | 49.50 | 54.00 |
| Povidone | 11.00 | 12.00 |
| Polyethylene oxide | 55.00 | 60.00 |
| Hypromellose | 8.25 | 9.00 |
| Silicon dioxide colloidal | 0.33 | 0.36 |
| Magnesium stearate | 5.50 | 6.00 |
| Purified water* | 33.00 | 39.00 |
| Coating A | | |
| Cellulose Acetate | 38.50 | 42.00 |
| Polyethylene Glycol 400 | 1.93 | 2.10 |
| Acetone* | 369.82 | 403.44 |
| Purified Water* | 81.18 | 88.56 |
| Coating B (optional) | | |
| Eudragit S 100 (Methacrylic Acid Copolymer, Type B) | 26.40 | 28.80 |
| Triethyl citrate | 2.86 | 3.12 |
| Talc | 14.74 | 16.08 |
| Isopropyl alcohol | 440.00 | 480.00 |
| Purified water | 26.40 | 28.80 |
| Coating C | | |
| Opadry Y 30 18084-A | 27.50 | 30.00 |
| Colorant | 0.33 | 0.36 |
| Purified Water* | 308.00 | 336.00 |

*denotes a component used during manufacture of the osmotic device but which is substantially absent in the final dosage form.

* denotes a component used during manufacture of the osmotic device but which is substantially absent in the final dosage form.

First, the core composition is prepared by placing carisoprodol, diclofenac sodium, mannitol, sodium chloride, povidone, polyethylene oxide and hypromellose in a high shear mixer and mix for 5 minutes. The granulation process is initiated by the gradual addition of a granulating solution containing polysorbate 20 and purified water to the high shear with continuous blending to produce a wet blend. Next, the wet blend is granulated and dried at 40-50° C. for 20 minutes in a fluid bed to remove the water. Then, the dry granules are screened through a 20 USP mesh screen for size reduction. Next, the screened granules are mixed with silicon dioxide colloidal and magnesium stearate, that have been previously passed through a 60 mesh screen, in a V-Blender during 5 minutes. This final blend is tabletted to provide the cores.

A first composition to cover the cores is prepared as follows: cellulose acetate and polyethylene glycol 400 are added to organic solvent and purified water, and mixed thoroughly to form a polymer solution. This solution is sprayed onto the tablets in a perforated pan coater to form film-coated cores. A 0.5 mm hole is drilled through the coating to provide perforated film-coated tablets.

The perforated film-coated cores can optionally be coated with an enteric coating prepared as follows: Eudragit S 100, talc, and triethyl citrate are added to purified water and isopropyl alcohol to form the coating suspension. This suspension is sprayed onto the tablets in a perforated pan coater to obtain enteric-coated osmotic device tablets.

A finish coat comprising Opadry and a colorant in purified water is applied onto the enteric-coated osmotic device tablets to obtain the final osmotic device tablets.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

We claim:

1. A rupturing controlled release device comprising: a) a core comprising an active agent and, optionally, at least one excipient, and b) a wall enclosing the core and having a weakened section and a preformed passageway there through, wherein the wall ruptures at the weakened section during use due to an increase of internal osmotic pressure of the core during use of the device to form a second passageway by breakage of the wall at a location spaced away from the preformed passageway such that active agent is released over an extended period of time from both passageways.

2. The controlled release device of claim 1, wherein the device is an osmotic device comprising: a) a core comprising at least one active agent, at least one osmopolymer, and, optionally, at least one excipient; b) a wall surrounding the core, the wall comprising a semipermeable membrane and optionally one or more other coatings or membranes; and c) a preformed passageway in the wall for at least initial release of the contents of the core, wherein the wall ruptures during due to an increase of internal osmotic pressure of the core during use of the device to form a spaced away second aperture by breakage of the wall such that the device provides an increased release rate of active agent after rupture as compared to before rupture of the wall, and the device provides a controlled release of the contents from the core.

3. The device of claim 1, wherein the release rate of active agent increases over time during use.

4. The device of claim 1 or 2, wherein at least 80% of the active agent is released by the end of use.

5. The device of claim 1 or 2, wherein the core comprises a swellable material, and the second passageway forms due to an increase of internal osmotic pressure of the core during use of the device.

6. The device of claim 1 or 2, wherein the preformed passageway is formed by mechanical means during manufacture of the osmotic device.

7. The device of claim 1 or 2, wherein the preformed passageway is plugged with a soluble material that dissolves during use of the osmotic device.

8. The device of claim 1 or 2, wherein the wall ruptures in a predetermined manner.

9. The device of claim 1 or 2, wherein the wall ruptures in a random manner.

10. The device of claim 1 or 2, wherein the second passageway is smaller than or approximates the size of the preformed passageway.

11. The device of claim 1 or 2, wherein the second passageway is larger than the preformed passageway.

12. The device of claim 1 or 2, wherein the second passageway forms at a predetermined location of the wall.

13. The device of claim 1 or 2, wherein the core comprises a nucleus that is coated with active agent and at least one excipient.

14. The device of claim 1, 2, or 3, wherein the exterior of the wall has at least one coating that effects the operation of the osmotic device in a manner according to the properties of the coating.

15. The device of claim 1 or 2, wherein the second passageway is formed more than about one hour after exposure of the device to an environment of use.

16. The device of claim 6, wherein the second passageway is formed more than about one hour after exposure of the device to an environment of use.

17. The device of claim 1 or 2, wherein the second passageway is formed more than about three hours after exposure of the device to an environment of use.

18. The device of claim 1 or 2, wherein the core comprises a first layer comprising the active agent and the at least one excipient and a second layer comprising a swellable material and/or an osmotic agent.

19. The device of claim 1 or 2, wherein the core comprises a nucleus comprising a swellable material and/or an osmotic agent and a coating surrounding the nucleus and comprising the active substance and the at least one excipient.

20. The device of claim 1 further comprising one or more coatings on the exterior of the wall, wherein the one or more coatings are independently selected at each occurrence from the group consisting of a drug-containing coating, a release rate modifying coating, a porous coating; a soluble coating, an insoluble coating, a semipermeable membrane; and a delayed release coating.

21. The device of claim 1 or 2, wherein the active agent is selected from the group consisting of albuterol, atenolol, acyclovir, amlodipine besylate, amoxicillin trihydrate, acetaminophen, allopurinol, atorvastatin calcium, aspirin, alprazolam, azithromycin dihydrate, caffeine monohydrate, candesartan cilexetil, carisoprodol, cimetidine, ciprofloxacin HCl, ciprofloxacin HCl monohydrate, citalopram, carbamazepine, carvedilol, celecoxib, clonazepam, clopidogrel bisulfate, diazepam, doxazosin mesylate, enalapril maleate, esomeprazole magnesium, eprosartan mesylate, fexofenadine HCl, fluconazole, fluoxetine HCl, galanthamine HBr, gemfibrozil, felodipine, glipizide, glyburide, hydrochlorothiazide, ibuprofen, lamotrigine, lansoprazole, loratadine, lorazepam, modafinil, memantine HCl, metronidazole, naproxen, nifedipine, nisoldipine, olanzapine, omeprazole, olmersartan medoxomil, paroxetine HCl, prednisone, pindolol, pioglitazone HCl, raloxifene HCl, ramipril, risperidone, rofecoxib, sertraline HCl, sildenafil citrate, simvastatin, tegaserod maleate, temazepan, telmisartan, trazodone HCl, triamterene, valsartan, vardenafil HCl, and zolpidem tartrate.

22. The device of claim 5, wherein the swellable material, when present, is selected from the group consisting of hydroxypropyl methylcellulose, poly(vinlypyrrolidone)-(vinyl acetate) copolymer, poly(vinylpyrrolidone), methyl methacrylate, calcium pectinate, poly(ethylene-vinyl acetate), hydroxylalkyl alkylcellulose, polyvinylalcohol, polyethylene oxide, a blend of gelatin and polyvinyl-pyrrolidone, gelatin, glucose, saccharide, povidone, copovidone, and polysaccharide gum.

23. The device of claim 18, wherein the swellable material, when present, is selected from the group consisting of hydroxypropyl methylcellulose, poly(vinlypyrrolidone)-(vinyl acetate) copolymer, poly(vinylpyrrolidone), methyl methacrylate, calcium pectinate, poly(ethylene-vinyl acetate), hydroxylalkyl alkylcellulose, polyvinylalcohol, polyethylene oxide, a blend of gelatin and polyvinyl-pyrrolidone, gelatin, glucose, saccharide, povidone, copovidone, and polysaccharide gum.

24. The device of claim 19, wherein the swellable material, when present, is selected from the group consisting of hydroxypropyl methylcellulose, poly(vinlypyrrolidone)-(vinyl acetate) copolymer, poly(vinylpyrrolidone), methyl methacrylate, calcium pectinate, poly(ethylene-vinyl acetate), hydroxylalkyl alkylcellulose, polyvinylalcohol, polyethylene oxide, a blend of gelatin and polyvinyl-pyrrolidone, gelatin, glucose, saccharide, povidone, copovidone, and polysaccharide gum.

25. The device of claim 2, wherein the at least one osmopolymer is selected from the group consisting of hydroxypropyl methylcellulose, poly(vinlypyrrolidone)-(vinyl acetate) copolymer, poly(vinylpyrrolidone), methyl methacrylate, calcium pectinate, poly(ethylene-vinyl acetate), hydroxylalkyl alkylcellulose, polyvinylalcohol, polyethylene oxide, a blend of gelatin and polyvinyl-pyrrolidone, gelatin, glucose, saccharide, povidone, copovidone, and polysaccharide gum.

26. The device of claim 1 or 2, wherein:
the core further comprises a surfactant, a diluent, an osmagent, and a binder; and
the wall comprises one or more cellulose esters and a plasticizer.

27. The device of claim 26, wherein:
the surfactant is selected from the group consisting of polysorbate, fatty amine oxides, fatty acid alkanolamides, and poly(oxyethylene)-block-poly(oxypropylene) copolymers, diethylene glycol monostearate, sodium lauryl sulfate, sorbitan monooleate, polyoxyethylene sorbitan fatty acid esters, polysorbate, bile salts, and glyceryl monostearate;
the diluent is selected from the group consisting of microcrystalline cellulose, lactose, sucrose, mannitol, cellulose, starch, sorbitol, dibasic calcium phosphate, and calcium carbonate;
the osmagent is selected from the group consisting of sodium chloride, salt, mannitol, acid, sugar, base, calcium salt, sodium salt, and lactose;
the binder is selected from the group consisting of poly(vinylpyrrolidone), povidone, sodium carboxymethylcellulose, alginic acid, poly(ethylene glycol), guar gum, polysaccharide, bentonite clay, sugar, poloxamer, collagen, albumin, gelatin, poly(propylene glycol), and poly(ethylene oxide);
the cellulose esters are selected from the group consisting of cellulose acetate, cellulose acetate phthalate, cellulose acetate trimelletate, cellulose acylate, and cellulose fatty acid ester; and
the plasticizer is selected from the group consisting of poly(ethylene glycol), low molecular weight polymer, citrate ester, triacetin, propylene glycol, glycerin, sorbitol lactate, ethyl lactate, butyl lactate, ethyl glycolate, and dibutylsebacate.

28. The device of claim 26, wherein:
the active agent is nifedipine present in an amount ranging from about 30-100 mg;
a surfactant is present in an amount ranging from about 0.10-7.50 mg;
a diluent is present in an amount ranging from about 20.00-270.00 mg;
an osmagent is present in an amount ranging from about 45.00-640.00 mg;
a binder is present in an amount ranging from about 10.00-150.00 mg;
at least one osmopolymer is present in an amount ranging from about 3.00-345.00 mg;
cellulose esters are present in an amount ranging from about 17.50-50.00 mg; and
a plasticizer is present in an amount ranging from about 0.50-7.00 mg.

29. The device of claim 26, wherein the active agent is selected from the group consisting of doxazosin, nifedipine, felodipine, carisoprodol, and a pharmaceutically acceptable salt thereof.

30. The device of claim 5, wherein:
the core further comprises a surfactant, a diluent, an osmagent, and a binder; and
the wall comprises one or more cellulose esters and a plasticizer.

31. The device of claim 30, wherein:
the surfactant is selected from the group consisting of polysorbate, fatty amine oxides, fatty acid alkanolamides, and poly(oxyethylene)-block-poly(oxypropylene) copolymers, diethylene glycol monostearate, sodium lauryl sulfate, sorbitan monooleate, polyoxyethylene sorbitan fatty acid esters, polysorbate, bile salts, and glyceryl monostearate;
the diluent is selected from the group consisting of microcrystalline cellulose, lactose, sucrose, mannitol, cellulose, starch, sorbitol, dibasic calcium phosphate, and calcium carbonate;
the osmagent is selected from the group consisting of sodium chloride, salt, mannitol, acid, sugar, base, calcium salt, sodium salt, and lactose;
the binder is selected from the group consisting of poly(vinylpyrrolidone), povidone, sodium carboxymethylcellulose, alginic acid, poly(ethylene glycol), guar gum, polysaccharide, bentonite clay, sugar, poloxamer, collagen, albumin, gelatin, poly(propylene glycol), and poly(ethylene oxide);
the cellulose esters are selected from the group consisting of cellulose acetate, cellulose acetate phthalate, cellulose acetate trimelletate, cellulose acylate, and cellulose fatty acid ester; and
the plasticizer is selected from the group consisting of poly(ethylene glycol), low molecular weight polymer, citrate ester, triacetin, propylene glycol, glycerin, sorbitol lactate, ethyl lactate, butyl lactate, ethyl glycolate, and dibutylsebacate.

32. The device of claim 30, wherein the active agent is selected from the group consisting of doxazosin, nifedipine, felodipine, carisoprodol, and a pharmaceutically acceptable salt thereof.

33. The device of claim 18, wherein:
the core further comprises a surfactant, a diluent, an osmagent, and a binder; and
the wall comprises one or more cellulose esters and a plasticizer.

34. The device of claim 33, wherein:
the surfactant is selected from the group consisting of polysorbate, fatty amine oxides, fatty acid alkanolamides, and poly(oxyethylene)-block-poly(oxypropylene) copolymers, diethylene glycol monostearate, sodium lauryl sulfate, sorbitan monooleate, polyoxyethylene sorbitan fatty acid esters, polysorbate, bile salts, and glyceryl monostearate;
the diluent is selected from the group consisting of microcrystalline cellulose, lactose, sucrose, mannitol, cellulose, starch, sorbitol, dibasic calcium phosphate, and calcium carbonate;
the osmagent is selected from the group consisting of sodium chloride, salt, mannitol, acid, sugar, base, calcium salt, sodium salt, and lactose;
the binder is selected from the group consisting of poly(vinylpyrrolidone), povidone, sodium carboxymethylcellulose, alginic acid, poly(ethylene glycol), guar gum, polysaccharide, bentonite clay, sugar, poloxamer, collagen, albumin, gelatin, poly(propylene glycol), and poly(ethylene oxide);
the cellulose esters are selected from the group consisting of cellulose acetate, cellulose acetate phthalate, cellulose acetate trimelletate, cellulose acylate, and cellulose fatty acid ester; and
the plasticizer is selected from the group consisting of poly(ethylene glycol), low molecular weight polymer, citrate ester, triacetin, propylene glycol, glycerin, sorbitol lactate, ethyl lactate, butyl lactate, ethyl glycolate, and dibutylsebacate.

35. The device of claim 33, wherein the active agent is selected from the group consisting of doxazosin, nifedipine, felodipine, carisoprodol, and a pharmaceutically acceptable salt thereof.

36. The device of claim 19, wherein:
the core further comprises a surfactant, a diluent, an osmagent, and a binder; and
the wall comprises one or more cellulose esters and a plasticizer.

37. The device of claim 36, wherein:
the surfactant is selected from the group consisting of polysorbate, fatty amine oxides, fatty acid alkanolamides, and poly(oxyethylene)-block-poly(oxypropylene) copolymers, diethylene glycol monostearate, sodium lauryl sulfate, sorbitan monooleate, polyoxyethylene sorbitan fatty acid esters, polysorbate, bile salts, and glyceryl monostearate;
the diluent is selected from the group consisting of microcrystalline cellulose, lactose, sucrose, mannitol, cellulose, starch, sorbitol, dibasic calcium phosphate, and calcium carbonate;
the osmagent is selected from the group consisting of sodium chloride, salt, mannitol, acid, sugar, base, calcium salt, sodium salt, and lactose;
the binder is selected from the group consisting of poly(vinylpyrrolidone), povidone, sodium carboxymethylcellulose, alginic acid, poly(ethylene glycol), guar gum, polysaccharide, bentonite clay, sugar, poloxamer, collagen, albumin, gelatin, poly(propylene glycol), and poly(ethylene oxide);
the cellulose esters are selected from the group consisting of cellulose acetate, cellulose acetate phthalate, cellulose acetate trimelletate, cellulose acylate, and cellulose fatty acid ester; and
the plasticizer is selected from the group consisting of poly(ethylene glycol), low molecular weight polymer, citrate ester, triacetin, propylene glycol, glycerin, sorbitol lactate, ethyl lactate, butyl lactate, ethyl glycolate, and dibutylsebacate.

38. The device of claim 36, wherein the active agent is selected from the group consisting of doxazosin, nifedipine, felodipine, carisoprodol, and a pharmaceutically acceptable salt thereof.

39. A method of preparing during use a coated controlled release device comprising a core comprising at least one active agent and, optionally, at least one excipient, a single or multi-layered wall enveloping the core, a preformed passageway in the wall, and a second passageway formed by breakage of a weakened section in the wall at a location spaced away from the preformed passageway due to an increase of internal pressure of the core during use, the method comprising the steps of:
a) providing a coated controlled release device comprising a core comprising: at least one active agent and, optionally, at least one excipient, a single or multi-layered wall enveloping the core, wherein at least one of the layers of the wall retains its physical integrity during release of active agent from the core of the device, a weakened section in the wall, and a preformed passageway through at least one layer of the wall, wherein the layer of the wall that comprises the preformed passageway is adapted to rupture and form the second passageway during use of the device; and b) exposing the device to an environment of use in which fluid is absorbed into the device thereby increasing the internal osmotic pressure within the device and causing breakage of the weakened section in the wall to form the second passageway at a location spaced away from the preformed passageway.

40. A method for treating a symptom, disorder and/or disease with at least one active agent, the method comprising the steps of:

a) providing at least one coated controlled release device comprising a core that comprises at least one active agent and, optionally, at least one excipient and that is substantially enclosed within a wall comprising a preformed passageway and a weakened section in the wall, wherein the weakened section of the wall is adapted to rupture during use of the device to form a second passageway at a region spaced away from the preformed passageway; and b) administering the device to a subject in need of such treatment such that the at least one active agent is released for a first period of time through the preformed passageway and then, after formation of the second passageway formed by tearing of the wall due to an increase of internal pressure of the core during use, the at least one active agent is released for a second period of time through one or both passageways.

41. The device of claim 2, wherein the one or more coatings is present and is a drug-containing coating.

42. The device of claim 41, wherein the active agent is a first drug from a first therapeutic class and the drug-containing coating contains a different second drug from a different therapeutic class.

43. The device of claim 42, wherein the first drug and second drug are independently selected at each occurrence from the group consisting of central nervous system agent, drug that acts on α-adrenergic receptors, electrolyte, ophthalmic agent, nutritional agent, antilipemic agent, phosphodiesterase inhibitor, β-blocker, diuretic, sympathomimetic agent, anti-Alzheimer disease agent, anti-Parkinson disease agent, muscle relaxant, local anesthetic, anti-spasmodic, muscle contractant, tranquilizer, antihypertensive agent, hypnotic agent, sedative, antipsychotic agent, estrogen antagonist-agonist agent, steroid, antidiabetic agent, antidepressant agent, anticonvulsant agent, psychic energizer, anticoagulant agent, antiasthma agent, antihistamine agent, decongestant, analgesic agent, anti-inflammatory agent, antiviral agent, antiparasitic agent, antibacterial agent, cardiovascular agent, nutrient, hematological agent, endocrine agent, metabolic agent, renal agent, genitourinary agent, respiratory agent, gastrointestinal agent, anti-infective agent, biologic agent, immunological agent, dermatological agent, antineoplastic agent and diagnostic agent.

44. The device of claim 43, wherein a) the anti-inflammatory drug is present and is selected from the group consisting of rofecoxib, celecoxib, etodolac, flurbiprofen, ibuprofen, ketoprofen, ketorolac, nabumetone, piroxicam, suprofen, tolmetin, zileuton, steroids, cyclooxygenase inhibitors, cortisone, hydrocortisone, betamethasone, dexamethasone, fluocortolone, prednisolone, phenylbutazone, triamcinolone, sulindac, indomethacin, salicylamide, naproxen, colchicine, fenoprofen, diclofenac, indoprofen, dexamethasone, allopurinol, oxyphenbutazone, probenecid and sodium salicylamide; and b) the muscle relaxant is present and is selected from the group consisting of alcuronium, alosetron, aminophylline, baclofen, carisoprodol, chlorphenesin, chlorphenesin carbamate, chlorzoxazone, chlormezanone, dantrolene, decamethonium, dyphylline, eperisione, ethaverine, gallamine triethiodide, hexafluorenium, metaxalone, metocurine iodide, orphenadrine, pancuronium, papaverine, pipecuronium, theophylline, tizanidine, tolperisone, tubocurarine, vecuronium, idrocilamide, ligustilide, cnidilide, senkyunolide, succinylcholine-chloride, danbrolene, cyclobenzaprine, methocarbamol, diazepam, mephenesin, methocarbomal, trihexylphenidyl, pridinol (pridinolum), and biperiden.

45. The device of claim 20, wherein the one or more coatings is present and is a drug-containing coating.

46. The device of claim 45, wherein the active agent is a first drug from a first therapeutic class and the drug-containing coating contains a different second drug from a different therapeutic class.

47. The device of claim 46, wherein the first drug and second drug are independently selected at each occurrence from the group consisting of central nervous system agent, drug that acts on α-adrenergic receptors, electrolyte, ophthalmic agent, nutritional agent, antilipemic agent, phosphodiesterase inhibitor, β-blocker, diuretic, sympathomimetic agent, anti-Dementia agent, anti-Alzheimer disease agent, anti-Parkinson disease agent, muscle relaxant, local anesthetic, anti-spasmodic, muscle contractant, tranquilizer, antihypertensive agent, hypnotic agent, sedative, antipsychotic agent, estrogen antagonist-agonist agent, steroid, antidiabetic agent, antidepressant agent, anticonvulsant agent, psychic energizer, anticoagulant agent, antiasthma agent, antihistamine agent, decongestant, analgesic agent, anti-inflammatory agent, antiviral agent, antiparasitic agent, antibacterial agent, cardiovascular agent, nutrient, hematological agent, endocrine agent, metabolic agent, renal agent, genitourinary agent, respiratory agent, gastrointestinal agent, anti-infective agent, biologic agent, immunological agent, dermatological agent, antineoplastic agent and diagnostic agent.

48. The device of claim 47, wherein a) the anti-inflammatory drug is present and is selected from the group consisting of rofecoxib, celecoxib, etodolac, flurbiprofen, ibuprofen, ketoprofen, ketorolac, nabumetone, piroxicam, suprofen, tolmetin, zileuton, steroids, cyclooxygenase inhibitors, cortisone, hydrocortisone, betamethasone, dexamethasone, fluocortolone, prednisolone, phenylbutazone, triamcinolone, sulindac, indomethacin, salicylamide, naproxen, colchicine, fenoprofen, diclofenac, indoprofen, dexamethasone, allopurinol, oxyphenbutazone, probenecid and sodium salicylamide; and b) the muscle relaxant is present and is selected from the group consisting of alcuronium, alosetron, aminophylline, baclofen, carisoprodol, chlorphenesin, chlorphenesin carbamate, chlorzoxazone, chlormezanone, dantrolene, decamethonium, dyphylline, eperisione, ethaverine, gallamine triethiodide, hexafluorenium, metaxalone, metocurine iodide, orphenadrine, pancuronium, papaverine, pipecuronium, theophylline, tizanidine, tolperisone, tubocurarine, vecuronium, idrocilamide, ligustilide, cnidilide, senkyunolide, succinylcholine-chloride, danbrolene, cyclobenzaprine, methocarbamol, diazepam, mephenesin, methocarbomal, trihexylphenidyl, pridinol (pridinolum), and biperiden.

49. The device of claim 47, wherein the first drug is a muscle relaxant, and the second drug is an anti-inflammatory drug.

50. The device of claim 49, wherein the first drug is a carisoprodol and the second drug is diclofenac.

51. The device of claim 47, wherein
a) the first drug is a muscle relaxant and the second drug is a selective or specific COX-II inhibitor agent;
b) the first drug is an analgesic agent and the second drug is an anti-inflammatory agent, wherein the analgesic agent and the anti-inflammatory agent is selected from the group consisting of an non-steroidal anti-inflammatory agent, a steroidal anti-inflammatory agent, an opioid receptor agonist agent, and a selective or specific COX-II inhibitor agent;
c) the first and second agents are antihypertensive agents selected from the group consisting of a calcium channel blocker agent, an angiotensin converting enzyme inhibitor agent, a diuretic agent and a beta-adrenergic antagonist agent;
d) the first and second agents are antidiabetic agents;
e) the first drug is a decongestant and the second drug is an antihistamine;
f) the first drug and the second drug are anti-incontinence drugs;
g) the anti-incontinence drugs are selected from the group consisting of oxybutynin, tolterodine, and darifenacin;
h) the first drug is an antidepressant and the second drug is for the treatment of Dementia;
i) the first drug is an antidepressant and the second drug is an antianxiety drug;
j) the first drug is an antidepressant and the second drug is an antipsychotic drug;
k) the first drug is an antianxiety drug and the second drug is for the treatment of Dementia;
l) the first drug is an antianxiety drug and the second drug is an antipsychotic drug;
m) the first drug is an antianxiety drug and the second drug is an antimanic drug;
n) the first drug is an antipsychotic drug and the second drug is an antimanic drug;
o) the first drug and the second drug are for the treatment of Dementia;
p) the first drug is for the treatment of Dementia and the second drug is an antianxiety drug;
q) the first drug is an anticonvulsant drug and the second drug is an antianxiety drug;
r) the first drug is an anticonvulsant drug and the second drug is an antipsychotic drug;
s) the first drug is an anticonvulsant drug and the second drug is for the treatment of Dementia;
t) the first drug is anticonvulsant and the second drug is an antimanic drug;
u) the first drug is an antiparkinsonian drug and the second drug is an antidepressant;
v) the first drug is an antiparkinsonian drug and the second drug is for the treatment of Dementia;
w) the first drug and the second drug are antiparkinsonian drugs;
x) the first drug and the second drug are mild CNS stimulants;
y) the first drug and the second drug are opioid analgesics;
z) the first drug is an opioid analgesic and the second drug is a non steroidal anti-inflammatory drug;
aa) the first drug and the second drug are non steroidal anti-inflammatory drugs;
bb) the first drug is a non steroidal anti-inflammatory drug and the second drug is a steroidal drug;
cc) the first drug and the second drug are antigout drugs; or
dd) the first drug and the second drug are antilimepic drugs.

52. The device of claim 21, wherein the active agent is carisoprodol.

53. The device of claim 52 further comprising a second active agent in the core.

54. The device of claim 53, wherein the second active agent in the core is diclofenac.

55. The device of claim 54 further comprising an enteric coating.

56. The device of claim 52 further comprising a drug-containing coating.

57. The device of claim 56, wherein the drug-containing coating comprises diclofenac.

58. The device of claim 57 further comprising carisoprodol in the drug containing coating.

59. The device of claim 57 further comprising an enteric coating.

60. The device of claim 58 further comprising an enteric coating.

* * * * *